US008926572B2

(12) United States Patent
Forsell

(10) Patent No.: US 8,926,572 B2
(45) Date of Patent: Jan. 6, 2015

(54) STIMULATION OF SEXUALLY RESPONSIVE TISSUE OF THE VULVA

(76) Inventor: Peter Forsell, Bouveret (CH)

( * ) Notice: Subject to any disclaimer, the term of this patent is extended or adjusted under 35 U.S.C. 154(b) by 403 days.

(21) Appl. No.: 13/123,573

(22) PCT Filed: Oct. 9, 2009

(86) PCT No.: PCT/EP2009/007289
§ 371 (c)(1),
(2), (4) Date: Apr. 11, 2011

(87) PCT Pub. No.: WO2010/040556
PCT Pub. Date: Apr. 15, 2010

(65) Prior Publication Data
US 2011/0288499 A1 Nov. 24, 2011

Related U.S. Application Data

(60) Provisional application No. 61/136,890, filed on Oct. 10, 2008.

(51) Int. Cl.
```
A61M 5/32      (2006.01)
A61M 5/142     (2006.01)
A61M 5/172     (2006.01)
A61M 5/44      (2006.01)
A61F 2/26      (2006.01)
A61M 5/14      (2006.01)
A61M 39/02     (2006.01)
```
(52) U.S. Cl.
CPC ......... *A61M 5/14276* (2013.01); *A61M 5/1723* (2013.01); *A61M 5/14212* (2013.01); *A61M 2205/3673* (2013.01); *A61M 5/44* (2013.01); *A61M 2205/82* (2013.01); *A61M 2210/1475* (2013.01); *A61F 2/26* (2013.01); *A61M 5/1428* (2013.01); *A61M 2205/353* (2013.01); *A61M 2205/3606* (2013.01); *A61M 5/1407* (2013.01); *A61M 2005/14284* (2013.01); *A61M 39/0208* (2013.01); *A61M 2209/045* (2013.01); *A61M 2205/364* (2013.01); *A61M 2205/8243* (2013.01); *A61M 2205/3613* (2013.01); *A61M 2205/366* (2013.01)
USPC ......................................... 604/272

(58) Field of Classification Search
CPC .......... A61F 2/26; A61M 2005/14284; A61M 2205/353; A61M 2205/3606; A61M 2205/3613; A61M 2205/364; A61M 2205/366; A61M 2205/3673; A61M 2205/82; A61M 2205/8243; A61M 2209/045; A61M 2210/1475; A61M 39/0208
USPC ............... 604/48, 39, 891.1, 272, 93.01, 523; 600/40
See application file for complete search history.

(56) References Cited

U.S. PATENT DOCUMENTS

2006/0129028 A1    6/2006 Krakousky
2011/0144468 A1*   6/2011 Boggs et al. .................. 600/373

FOREIGN PATENT DOCUMENTS

WO    WO 00/33825      6/2000
WO    WO 2007/051563   5/2007

OTHER PUBLICATIONS
International Search Report for PCT/EP2009/007289, mailed Apr. 23, 2010.

*Primary Examiner* — Kami A Bosworth
*Assistant Examiner* — Imani Hayman

(57) ABSTRACT

A female external genitalia stimulation system, in particular clitoris erection stimulation system, comprises a fully implantable drug delivery device for delivering a drug in relation to a erectile tissue to achieve erection thereof. The drug delivery device may comprise a catheter adapted to be implanted in the corpora cavernosa of a clitoris or in close proximity thereto in order to deliver drugs through said catheter. Alternatively, one or more infusion needles may be disposed within and implanted along with one or more housings adjacent the patient's left and right corpora cavernosa. A reservoir and a pump may also be implanted inside the patient's body to supply the infusion needle with infusion liquid. A drive unit also adapted for implantation inside the patient's body is arranged for advancing and retracting the tip end of the infusion needle such that it penetrates the housing at least in two different penetration areas either simultaneously or in immediate time succession, thereby injecting drugs along with the infusion liquid into the patient's body for stimulating erectile tissue, in particular for stimulating clitoris erection.

25 Claims, 29 Drawing Sheets

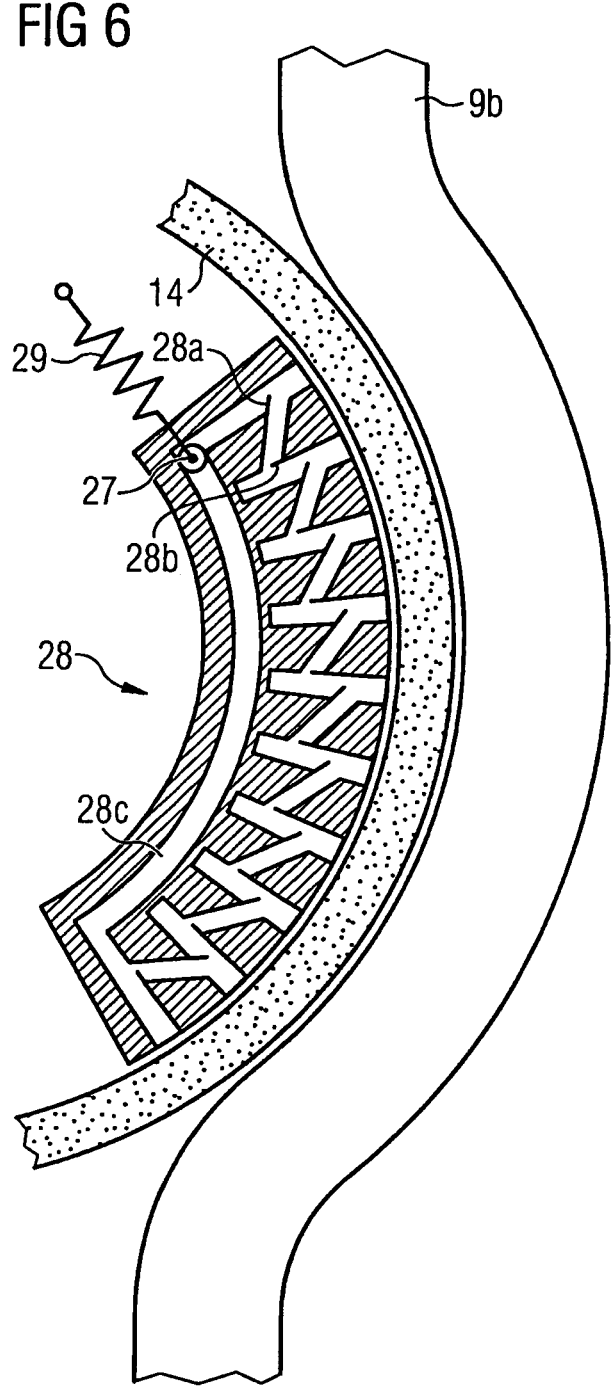
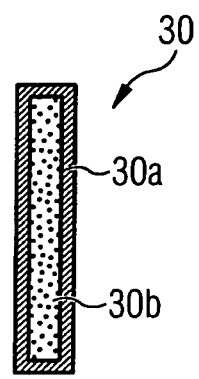
FIG 6
FIG 7

STIMULATION OF SEXUALLY RESPONSIVE TISSUE OF THE VULVA

This application is the U.S. national phase of International Application No. PCT/EP2009/007289, filed 9 Oct. 2009, which designated the U.S. and claims the benefit of U.S. Provisional No. 61/136,890, the entire contents of each of which are hereby incorporated by reference.

BACKGROUND OF THE INVENTION

The invention relates to a female stimulation system for stimulating sexually responsive tissue of the vulva, in particular an erection or lubrication stimulation system. The present invention relates to the infusion of a drug into a female's body in order to stimulate the external genitalia for sexual purposes, in particular to stimulate erectile tissue, such as of the clitoris, the anterior labia minora and/or the bulbs of the vestibule, and/or to stimulate activity of the vestibular glands in order to sectrete mucus into the vestibule, which moistens the labia and the vestibule.

A lot of attention has been given to male sexual disorders including impotency. This has lead to the availability of a number of treatment options for males, including pharmaceuticals such as Viagra. In contrast, there is a lack of therapies for treating female sexual dysfunctions. Female sexual dysfunction such as disorders of sexual desire, arousal or orgasm is a common problem, affecting up to 43% of all women (Pauls et al, Obstret Gynecol Surv, 2005 60(3):3196-205). Both biological and psychological factors contribute to female sexual dysfunctions. Available treatments include psychological counselling to pairs or individuals. Where side effects of medication contributes to female sexual dysfunctions, altering medication or dosage may help. However, there is a need for improved treatment of female sexual dysfunctions.

During sexual arousal of the female, vasocongestion of the pelvic region leads to engorgement of the genitalia with blood leading to swelling of the external genitalia and erection of the clitoris. More specifically, connections between arteries and veins are closed (arteriovenous anastomoses) so that blood which is normally able to bypass the empty spaces or sinuses of the clitoris' corpora cavernosa is retained in the clitoris. In the female, the corpus cavernosa are two paired symmetrical extensions of the clitoris. Enlargement of the clitoris by engorgement of the corpora cavernosa is an important step during sexual arousal of the female since it can increase sexual excitement.

The main vessels supplying the blood to the cavernous spaces in the erectile tissue of the corpora cavernosa are the deep arteries of the clitoris. They are therefore heavily involved in the erection of the clitoris. They give off numerous branches—the helicine arteries—that open directly into the cavernous spaces. When the clitoris is flaccid, these arteries are coiled, restricting blood flow. However, the smooth muscle in the coiled helicine arteries relaxes as a result of parasympathetic stimulation. In their relaxed state, the helicine arteries straighten, enlarging their lumina and allowing blood to flow into and dilate the cavernous spaces in the corpora of the clitoris at arterial pressure. In combination with the ischiocavernosus muscles compressing the veins egressing from the corpora cavernosa, the erectile bodies of the clitoris become enlarged and turgid, and an erection occurs.

The clitoris is highly sensitive. Hand held or other external devices that stimulate the clitoris are well-known. For example U.S. Pat. No. 7,081,087B2 discloses a sexual aid that vibrates. There has been proposed a device for treating female sexual dysfunctions that applies a vacuum or suction to the clitoris. This will create a negative pressure that promotes the engorgement of the clitoris with blood (Hovland Claire, U.S. Pat. No. 6,464,653 B1). In addition, local administration of prostaglandins to the female genitalia in order to treat female sexual dysfunctions has been described in U.S. Pat. No. 6,486,207. Also, the implantation of an electrode that stimulates the peripheral nerves of the vulva has been described in US 2008/0103544.

Erection of the clitoris is accompanied by lubrication of the vagina. The bulbospongiosus muscle assists in the erection of the clitoris and the bulbs of the vestibule, and further compresses the greater vestibular gland so as to secrete mucus into the vestibule so as to lubricate the vagina.

It is the object of the present invention to improve the sexual stimulation of sexually responsive tissue of the vulva in a manner that is convenient for the patient.

SUMMARY OF THE INVENTION

The essence of the invention lies in injecting a drug into the patient's body so as to sexually stimulate sexually responsive tissue of the vulva using a fully implantable drug delivery device for delivering the drug in relation to the female's sexually responsive tissue of the vulva to achieve sexual stimulation thereof, in particular an erection and/or a lubrication. The term "sexually responsive tissue of the vulva" refers to sexually responsive tissue of the female's vulva including but not limited to: the clitoris, labia minora, labia majora, corpora cavernosa, vagina and bulbs of the vestibule.

An advantage of the implantation of a stimulating device is that it is always at hand and can conveniently be switched on before sexual intercourse. Hand held devices are more likely to cause embarrassment. Also, the fully implantable drug delivery device is convenient for the patient, as he does not have to administer the drug from outside the body.

In general, the system may be adapted to stimulate an erectile tissue part of the sexually responsive tissue of the vulva to achieve engorgement of blood to cause erection of the erectile tissue. Alternatively, the system may be adapted to stimulate a lubrication part of the sexually responsive tissue of the vulva to achieve lubrication of sexually responsive tissue of the vulva. In particular, the system may be adapted to stimulate the nerval system of the sexually responsive tissue of the vulva to achieve engorgement of blood to cause erection of the erectile tissue or to achieve stimulation of the lubrication part of the sexually responsive tissue of the vulva to achieve lubrication of sexually responsive tissue of the vulva. The term "erectile tissue" refers to tissue of the female sexual organs that before or during sexual intercourse are filled with blood including, but not limited to, the corpora cavernosa of the clitoris and the vestibular bulbs and likewise refers to extensions of said tissue including, but not limited to, blood vessels and the surrounding tissues. The term "lubrication part of the sexually responsive tissue of the vulva" refers to any part of the vulva involved in the lubrication of vagina and the vestibule or associated areas of the sexually responsive tissue of the vulva, and particularly refers to the vestibular glands.

More specifically, the drug may be supplied, more specifically injected, from inside the patient's body into both the right and left corpus cavernosum and/or into the two deep arteries thereof and/or into the bulbs of the vestibule and/or possibly into muscle tissue regulating blood flow through the right and left corpus cavernosum and/or regulating blood flow through the bulbs of the vestibule, such as the ischiocavernosus and bulbospongiosus muscles, and/or into tissue in close proximity to the clitoris, labia minora and/or bulbs of the vestibule, so as to cause erection of the corresponding erectile tissue.

According to a first, most simple embodiment, the drug delivery device comprises at least one catheter adapted to be implanted outside the corpora cavernosa in close proximity thereto so as to supply the drugs through the catheter. Alternatively, the at least one catheter may be adapted to be implanted in at least one corpus cavernosum so as to supply the drugs directly into the corpus cavernosum through the catheter. The latter alternative is more complicated to implant, but more efficient in use.

According to a preferred, somewhat more complex embodiment, the drug delivery device comprises at least one infusion needle for injecting the drugs, wherein the infusion needle is permanently implanted at an appropriate location inside the patient's body. Due to the permanent implantation of the infusion needle, the injection will always occur at the proper location, said location being selected such that the drug is most effective. While there are many conceivable technical variations for injecting the drug through the infusion needle into the patient's body, such injections are definitely more convenient for the patient once the infusion needle has been implanted as compared to the alternative of injecting the drug into the relevant tissue material manually from outside the patient's body. In particular, the infusion needle may be integrated in the above-mentioned catheter.

The infusion needle of the drug delivery device may be adapted to be placed outside the corpora cavernosa in close proximity thereto and may further be adapted to change its position outside the corpora cavernosa, when the drug delivery device is implanted. Thus, whenever the needle's position is changed outside the corpora cavernosa, drugs are delivered through the infusion needle into a region outside the corpora cavernosa. Alternatively, the at least one infusion needle being placed outside the corpora cavernosa may be adapted to be advanced into and retracted from at least one of the corpora cavernosa. In this case, whenever the needle is advanced into a corpus cavernosum, the drugs are delivered through the infusion needle into the corpus cavernosum. This latter alternative is more efficient in use.

Most preferably, one or more infusion needles are arranged at least with the tip end or ends thereof disposed within (at least one) housing so as to penetrate the housing's outer wall or walls in at least one penetration area, more preferably in two or more different penetration areas. Arranging the infusion needle's tip end in a housing prevents any fibrosis from growing into the infusion needle. Preferably, the needle or needles are fully accommodated in said housing. Where more than one needle is provided, the needles—or at least the tip ends thereof—may be arranged in separate housings. The housing or housings are adapted for implantation inside the patient's body adjacent the two corpora cavernosa and/or adjacent the two deep arteries thereof and/or adjacent the bulbs of the vestibule and/or adjacent muscle tissue regulating blood flow through the patient's left and right corpus cavernosum and/or regulating blood flow through the bulbs of the vestibule, such as the ischiocavernosus and bulbospongiosus muscles, and/or adjacent to tissue in close proximity to the clitoris, labia minora and/or bulbs of the vestibule. Where the at least one infusion needle is arranged for penetrating the at least one housing in two or more different penetration areas, the distance between the different penetration areas to be penetrated by the at least one infusion needle is selected such that the respective parts of the patient's body are pierced whenever the drug is to be injected. As will be described below, two or more infusion needles may be provided in a single housing or in different housings in order to inject the drug in the two or more different penetration areas, or a single infusion needle may be provided in a single housing along with an appropriate drive unit for displacing the tip end of the infusion needle so as to penetrate the single housing's outer wall in the respective different penetration areas.

Furthermore, according to the invention, at least one drive unit, which is also adapted for implantation inside the patient's body, is coupled to the at least one infusion needle so as to—at least—advance and retract the tip end of the at least one infusion needle in such a way that it penetrates at least two of said different penetration areas within the housing's or housings' outer wall, so as to allow for stimulation of tissue erection and/or muscle contraction by injecting the substance through said at least two different penetration areas via the at least one infusion needle. For instance, the at least one infusion needle may be arranged for penetrating the at least two different penetration areas either simultaneously (e.g. where a plurality of needles, i.e. at least two needles, are provided) or in immediate time succession (e.g. where a single needle is provided).

Preferably, a single command or single action from the patient is sufficient for injecting the substance through the at least two penetration areas, either due to a corresponding mechanical structure of the drive unit or due to a suitably configured control unit controlling the drive unit. This will make the handling of the system easy for the patient.

Where two different penetration areas are pierced in immediate time succession, the time delay between the penetration of the first and the second of the penetration areas is preferably as short as possible, more preferably less than 120 seconds, and most preferably less than 60 seconds. This can be achieved by means of a properly controlled drive unit. A longer time delay would be inconvenient for the patient. Therefore, it is preferred that, once the infusion needle has been retracted from a first of the two penetration areas, it is immediately advanced to the second of the penetration areas.

While it is possible according to one aspect of the invention to actively open the outer wall or walls of the at least one housing for allowing the infusion needle to penetrate the outer wall, it is preferred according to another aspect of the invention to arrange the needle so as to penetrate the outer wall by piercing through the outer wall. For that purpose, the outer wall may either comprise flaps to be pushed aside by the infusion needle as the infusion needle is advanced, or the outer wall may be made at least in the penetration areas from a material which is self-sealing in respect of penetrations resulting from the at least one infusion needle. While the entire housing may be made from the self-sealing material, it is advantageous for stability reasons if the self-sealing material forms at least one window area in the outer wall, the window area being positioned for penetration by the tip end of the at least one infusion needle. The window area may be formed by a self-sealing penetration membrane which is preferably integrated in the outer wall by press fitting it into the outer wall.

Typically, the self-sealing material would be made from a polymer material which preferably comprises silicone. Other biocompatible polymer materials, such as polyurethane and the like, may be employed as well.

The self-sealing material may also be a composite material. A particularly preferred embodiment of such composite material comprises at least one outer shape-giving layer and a self-sealing soft material contained within the outer layer. Thus, the outer layer forms a shell for the soft material. The outer layer may be made from a biocompatible polymer, such as one of those polymers mentioned above, and preferably the self-sealing soft material may be a gel.

Instead of a self-sealing material, the part of the outer wall to be penetrated by the infusion needle may comprise one or more flaps in the penetration areas through which the infusion needle or needles can pass. This can reduce the force needed for the infusion needle to penetrate the outer wall, as compared to the penetration of a self-sealing membrane. The flap is preferably arranged to be pushed aside by the infusion needle upon advancement of the infusion needle.

Alternatively, the outer wall may comprise at least one door in the penetration areas. A drive is connected to the door for actively opening the door so as to allow for the infusion needle to be advanced through the opened door. Again, the door may comprise a flap, such as a resilient, normally closed flap. It is particularly preferred if the drive connected to the door forms part of the drive unit coupled to the infusion needle. More specifically, the arrangement may be such that advancement of the infusion needle by means of the drive unit simultaneously causes the drive to open the door.

Where a single housing is provided for the at least one infusion needle (or at least for the tip ends thereof) or where two or more penetration areas are arranged in a single housing, the penetration areas may be arranged in the housing so that they can be placed either adjacent to both the right and left corpus cavernosum of the patient's clitoris and/or adjacent the two deep arteries of the right and left corpus cavernosum and/or adjacent the bulbs of the vestibule and/or adjacent to muscle tissue regulating blood flow through the right and left corpus cavernosum and/or regulating blood flow through the bulbs of the vestibule and/or in sufficiently close proximity to another type of tissue allowing both the first and second corpus cavernosum to become turgid when the particular drug is injected thereinto.

The at least one infusion needle preferably has a tube-like body closed at the tip end and provided with a laterally arranged delivery exit port for delivery of the drug into the particular body part. Therefore, the needle will not cut out any material but will simply divide it during penetration. Thus, when the needle penetrates any material, such as fibrosis and/or the self-sealing penetration membrane, there will be no material entering and blocking the drug delivery passageway.

As mentioned above, a separate infusion needle may be provided for each of the two or more penetration areas. Thus, where injection is desired to occur in only two different areas to provoke tissue erection, two separate infusion needles may be advanced through the corresponding penetration area of the respective housing—preferably simultaneously—and retracted again after injection.

According to a preferred embodiment of the invention, a plurality of two or more infusion needles are provided for each of the different penetration areas and arranged for penetrating different penetration sites within each of said different penetration areas. This allows for penetrating different sites within each penetration area at different times, thereby giving the human tissue time to recover from the piercing by the infusion needle. This can be achieved with a drive unit suitably configured to advance and retract one infusion needle in each of said different penetration areas at one time, and to advance and retract a different infusion needle in each of said different penetration areas at a different time.

The system may further comprise at least one reservoir adapted for implantation inside the patient's body, the reservoir being in fluid connection with the at least one infusion needle so as to supply to the infusion needle the substance to be injected into the patient's body. Also, at least one pump, which is also adapted for implantation inside the patient's body, may be provided to advance the substance from the reservoir to the at least one infusion needle.

Since it is preferred for reasons of space constraints to implant the reservoir remote from the injection areas, it can be advantageous to employ long infusion needles that are flexibly bendable. The tip ends of such infusion needles would then be arranged within at least one first housing so as to penetrate the outer wall thereof upon advancement of the long infusion needle. The at least one first housing accommodating the tip end of such long infusion needle or needles can be arranged in close proximity to the injection area so that the tip end can penetrate the outer wall of the first housing upon advancement of the long infusion needle. The respective other end of the infusion needle or needles, i.e. the infusion needle's rear end, is arranged in at least one second housing which can be implanted inside the patient's body remote from the first housing in an area with less space constraints. The injection needle would be sufficiently long to bridge the distance from the second housing for remote implantation to the first housing and further through the first housing up to the outer wall of the first housing to be penetrated by the needle. The long and flexibly bendable infusion needle may be guided within a suitable sheath. Since the rear end of the long infusion needle or needles is remotely implanted within the patient's body, other components of the system cooperating with rear end of the long infusion needle may also be implanted remote from the injection area, such as the reservoir for storing the substance to be injected, the pump for advancing the drug from the reservoir to the infusion needle and further through the needle into the patient's body, and a motor for actuating the system's active parts. In a particularly preferred embodiment, the tip end of the long infusion needle is advanced by advancing the entire needle from the infusion needle's rear end. In this context, it is particularly advantageous to also arrange at least a part of the drive unit, preferably the entire drive unit, for advancing and retracting the tip end of the infusion needle remote from the injection area, preferably within the second housing and even more preferably in a common housing with the remotely implanted reservoir. More preferably, most or all of the active parts, such as a motor, pump and the like, may be accommodated in the remotely implanted second housing, whereas the first housing only includes passive elements.

A drive unit according to the present invention includes not only the drive itself, such as an electric motor, but also those components which are involved in transforming the driving energy provided by the drive into movement of the at least one needle, such as transmission gears and the like.

For instance, in the case of the long flexibly bendable infusion needle, the drive unit may be such that the infusion needle is advanced and/or retracted by turning the infusion needle or by turning an element cooperating with the infusion needle. More specifically, the drive unit for advancing and retracting the infusion needle may comprise a screw drive connection. For instance, the drive of the drive unit may turn a screw threadingly engaged with a rack coupled to the infusion needle so that rotation of the screw will cause the infusion needle to be advanced or retracted. The screw and rack of the screw drive connection are preferably accommodated in the remotely implanted second housing but may also be arranged in the housing accommodating the tip end of the needle. Instead of the screw, the infusion needle itself may be rotated by means of a suitable drive so that threading on the needle engaging a fixedly mounted rack causes the infusion needle to advance or retract upon rotation of the infusion needle. Between the first and second housings, the infusion needle is preferably guided in a sheath, so as to reduce friction and prevent growth of fibrosis that might hinder movement of the needle.

According to a particularly preferred aspect of the invention, the tip end or ends of the at least one infusion needle are laterally movable, so as to vary the penetration sites within a particular penetration area of the at least one housing's outer wall, thereby varying the injection site within the particular injection area in the patient's body. As set out above, frequent piercing of the same body part may cause irritation, eventually making further piercing difficult or even impossible. Variation of the injection site by laterally displacing the needle upon each injection cycle may overcome such problems. Accordingly, the at least one drive unit in the common housing is preferably configured to laterally displace the tip end or ends of the at least one infusion needle to different penetration sites within a penetration area. More specifically, where two or more infusion needles are provided for penetrating two or more different penetration areas, the drive unit is preferably configured to laterally displace the tip ends of the infusion needles simultaneously. This can be achieved e.g. by jointly mounting the tip ends of the infusion needles on a movable carriage of the drive unit, such as a turntable and/or a shuttle, possibly in the form of a slide. Thus, the drive unit for advancing and retracting the tip end or ends of the at least one infusion needle is preferably configured so as to also laterally displace a tip end each time the tip end is advanced or retracted.

Thus, the lateral displacement and the advancement/retraction of the tip end of an infusion needle is coordinated. The lateral displacement of the tip end of the infusion needle may take place before and/or after an injection. The mechanism may be such that after a certain number of lateral displacements or after lateral displacement over a predefined distance, the tip end of the infusion needle is laterally returned to its initial position so that the next number of infusions will take place again at locations that have previously been penetrated by the needle. It is even preferred to configure the drive unit such that the tip end of the infusion needle is displaced in at least two different lateral directions within one penetration area. For instance, when the infusion needle has laterally returned to its initial position, the next number of infusions may take place somewhat laterally offset above or below the first number of penetration sites. This permits a two-dimensional array of penetration sites to be obtained. In particular, the drive unit may be configured to displace the tip end of the infusion needle along a curved path, which will result in a three-dimensional array of penetration sites if the needle is displaceable in different lateral directions.

Where two or more infusion needles are provided for penetrating two or more different penetration areas, the infusion needles or, in the case of the aforementioned long and flexibly bendable infusion needles, at least the tip ends thereof may be contained in a common housing in spaced apart relationship, with the drive unit being configured to advance and retract the tip ends of the infusion needles so as to penetrate the outer wall of the common housing in said at least two different penetration areas, again preferably simultaneously. The infusion needles—or at least the tip ends thereof—may be arranged one above the other within the common housing. Generally speaking, it is preferable in such a situation that the direction of lateral displacement of the tip ends of the infusion needle within different penetration areas is different from, in particular perpendicular to, the direction of distance between the different penetration areas. Alternatively, where the infusion needles are arranged with great lateral distance between each other, the direction of lateral displacement of the tip ends of the infusion needles within each of two different penetration areas may generally be the same as the direction of distance between the two different penetration areas. Placing the two or more injection needles—or at least the tip ends thereof—in a common housing simplifies the procedure of fixing the needles in place close to the injection areas.

Furthermore, a single drive unit may be used for advancing and retracting the tip ends of the plurality of infusion needles, this making the entire system less voluminous. The use of a single drive unit is particularly advantageous where a major part of the drive unit is also contained in the common housing, i.e. where a major part of the drive unit is also to be implanted close to the very constrained injection area.

Instead of providing two or more infusion needles for penetrating two or more different penetration areas, it is likewise possible to provide a single infusion needle or the tip end of a single needle within the housing and to implant the housing within the patient's body adjacent the two or more injection areas. In this case, the drive unit may be configured so as to laterally displace the tip end of the single one infusion needle between various lateral positions such that the infusion needle can penetrate the housing's outer wall in the different penetration areas. The distance of lateral displacement of the single infusion needle between the different penetration areas would amount to 3 mm, 4 mm, 5 mm or even more upon each successive injection. Such successive injections are preferably in immediate time succession, preferably not exceeding 120 seconds between two injections, more preferably not exceeding 60 seconds. Most preferably, the drive unit will be adapted to initiate advancement of the one infusion needle to a second one of the plurality of penetration areas once it has been retracted from a first one of the penetration areas.

An implantable infusion device comprising a single, laterally displaceable infusion needle contained within a housing so as to penetrate the housing's outer wall at different penetration sites is generally known from WO 2007/051563. However, this prior art infusion device is not aimed at being used for the stimulation of tissue erection. Also the prior art device is neither intended nor configured for injecting drugs simultaneously or quasi-simultaneously in immediate time succession in two or more different injection areas. The drive unit of the prior art device is instead configured to administer the drug at a different penetration site of a single injection area at each time of operation. For instance, the prior art device may be placed along a blood vessel so as to inject drugs at different injection sites within a single injection area of the blood vessel. Thus, the distance of lateral displacement of the tip end of the infusion needle between one injection and a next following injection is not configured in the prior art device such that different injection areas within the patient's body could be reached.

Turning back to the present invention, it is again preferable, when the patient desires to achieve another erection of e.g. the clitoris at a later point of time, that the single infusion needle does not penetrate the same penetration site within the particular penetration area of the housing's outer wall, but that the drive unit is configured to laterally displace the tip end of the one infusion needle to different penetration sites within each of the different penetration areas. Again, the direction of lateral displacement of the tip end of the one infusion needle within each of the different penetration areas may either be the same as the direction of lateral displacement of the tip end of the infusion needle between the different penetration areas, or may be different from, in particular perpendicular to, the direction of lateral displacement of the tip end of the infusion needle between the different penetration areas. Depending upon the particular configuration of the system, this may be achieved with a single, multifunctional drive unit or with a plurality of different drive units suitably arranged to work in coordinated fashion. Even a combination of these alternatives is possible. For instance, when after a number of infusion cycles the single infusion needle has laterally returned to its initial position, the next number of infusions within the same penetration area may take place somewhat laterally offset above or below the first number of penetration sites. Thus, a two-dimensional array of penetration sites can be obtained in each penetration area, thereby keeping the maximum dimensions of the penetration areas at a minimum.

Where the housing or at least the window area thereof is formed spherically, even a three-dimensional array of penetration sites through the housing's outer wall can be obtained by means of a suitably adapted drive unit for the needle displacement. This greatly increases the system's flexibility of use.

Regardless of the number of needles involved and regardless of the particular penetration site array to be achieved, it is preferable to configure the drive unit such that the lateral displacement of the tip end of the infusion needle or needles is achieved automatically during advancement and/or retraction of the tip end of the needle or needles. For instance, where the infusion needle is mounted on a movable carriage for the lateral displacement of the tip end of the needle, such as on a turntable or a shuttle, e.g. in the form of a slide, the drive unit may comprise a stepper which is adapted to automatically advance the movable carriage a predefined distance upon each advancement and/or retraction of the infusion needle.

Now, turning to the reservoir, it should be considered that long term storage is not possible with many currently available drugs, this being particularly true of drugs stimulating erection of sexual tissue material, such as the clitoris. Such drugs are generally known for stimulating penis erection, the male's penis being to a large extent comparable in structure with the female's clitoris. Where long term storage is desired, the drug to be injected would typically be provided as a first substance and mixed with a second substance for injection shortly before the injection is performed. Therefore, according to a preferred embodiment of the present invention, the reservoir of the system comprises at least one first compartment, e.g. for accommodating an infusion liquid such as a saline solution, and at least one second compartment, e.g. containing a drug, in particular a drug in dry form, for mixing with the infusion liquid of the first compartment. The drug may be in powder form and, more specifically, may be a freeze-dried drug. In particular, the drug contained in the second compartment would be a drug for stimulating clitoris erection. A mixing chamber may be provided for mixing the substance from the first compartment with the substance from one or more of the at least one second compartment.

The number of the second compartments may be huge, such as 50 or more, in particular 100 or more. This would not constitute a particular problem in terms of space constraints since the amount of drugs required for each stimulation of clitoris erection is extremely little and would amount to a few micrograms. Furthermore, the reservoir may be adapted for implantation within the patient's body remote from the housing containing the needle, such as close to the symphyseal bone. There is a lot of space available above the patient's symphyseal bone, and the drugs could be delivered to the tip end of the needle through an appropriate conduit. If desired, one can inject pure saline solution after the drug injection has been completed so as to clean the conduit and needle from any drug residue. Such cleaning injection could be done through a different penetration area of the housing's outer wall into tissue of the patient which would not affect the stimulation of an erection.

Preferably, the second compartments containing the drug are liquid-tightly sealed against the first compartment, with a mechanism being provided for individually opening a connection between the second compartments and the first compartment.

According to a preferred embodiment, the second compartments are mounted in a plate so as to open towards a first side of the plate and the opening mechanism is adapted to act on the second compartments from a second side of the plate opposite the first side of the plate so that the compartments open to the first side of the plate. Thus, the second compartments may be pushed from their rear side (second side of the plate) so as to open frontward into e.g. a mixing chamber in which the content of the opened second compartments mixes with the content of the first compartment of the reservoir, such as with saline solution. More specifically, the second compartments may be mounted in the plate as displaceable drug containers and the opening mechanism may be adapted to displace the drug containers such that they deliver their drug contents in the manner described.

Alternatively, the plate may be rotatable so as to allow the drug containers to be brought into alignment with a conduit upon rotation of the plate. Thus, when the drug is brought into alignment with such conduit, it may be mixed with e.g. saline solution pumped through the conduit towards the infusion needle.

According to another preferred embodiment, the second compartments are mounted on a tape wound up on a reel. A plurality of rows of the second compartments may be arranged on the tape in side-by-side relationship in a direction different to the winding direction of the tape. This way, the length of the tape can be reduced. It is particularly preferable if the tape is contained in a replaceable cassette. Thus, when all of the second compartments of the tape are emptied, the tape can be easily replaced by replacing the cassette.

As mentioned above, while the reservoir may generally be part of the housing accommodating the at least one infusion needle, it is preferred to arrange the reservoir separate from the housing for remote implantation within the patient's body.

At least a section of a periphery of the first compartment of the reservoir may be made from a flexible material permitting volume changes of the first compartment by deformation of the flexible material as infusion liquid is filled into or drawn out of the reservoir. Thus, the reservoir may be of balloon type. The flexible material may comprise a polymer membrane. A bellows construction is preferable having pre-bent creases to reduce long term degradation.

According to a particular embodiment, drawing liquid from the reservoir may cause a pressure decrease in at least part of the reservoir so that a negative pressure is attained as compared to the pressure in front of the infusion needle. For instance, the first compartment of the reservoir may comprise a gas chamber and a liquid chamber, said chambers being separated by a membrane, e.g. the polymer membrane. When liquid is drawn from the liquid chamber, the pressure in the gas chamber will decrease accordingly.

The reservoir may have an injection port for injecting liquid from outside the human body into the implanted reservoir. That way, the reservoir implanted in the patient's body along with the drug delivery device may be kept relatively small since the reservoir can be refilled easily at appropriate time intervals, possibly with a doctor's aid.

Preferably, the injection port comprises a self-sealing material in respect of penetrations caused by a replenishing syringe that would be typically used to refill the reservoir through the patient's skin. It is preferable to implant the self-sealing injection port of the reservoir subcutaneously in the patient's body so that it is easily accessible for refill by means of the syringe.

The conduit or conduits for connecting the remotely implanted reservoir with the infusion needle or needles should have a length sufficient to bridge the distance between the patient's symphyseal bone and the inferior fascia of the patient's urogenital diaphragm, where the housing is preferably to be placed. Accordingly, the conduit should have a length of 10 cm or more.

While it has already been pointed out that drugs, in particular the drugs for stimulating clitoris erection, may degrade upon long term storage, another important influence on drug degradation is the storage temperature. Some drugs have to be stored in a refrigerator at low or at least moderate temperature. A preferred embodiment of the invention therefore provides for a cooling device for keeping the content within at least one compartment of the reservoir at a temperature below 37° C. This can be achieved with relatively little energy supply if the amount of drugs to be cooled is extremely little, as explained above, and if furthermore the drug compartment within the reservoir is thermally insulated. For instance, the reservoir may be comprised in an insulation chamber.

It is preferred to provide the cooling device with a heat exchanger for exchanging with the patient's body heat generated by the cooling device. Such heat exchanger may be implanted within the patient's body remote from the cooling device to safely dissipate the heat energy in an area where it cannot adversely affect the content of the reservoir.

The cooling device can be of a variety of different types. According to a first embodiment, the cooling device may contain at least two different chemicals reacting with each other, thereby consuming thermal energy which energy is drawn from the contents within the reservoir so that a cooling effect on the contents is achieved. The two chemicals may be provided in separate chambers and a flow control device may be provided to bring together certain amounts of the two different chemicals so as to control the amount of thermal energy drawn from the contents within the reservoir.

According to a second embodiment, the cooling device may comprise at least one Peltier element. A Peltier element is an electrothermal converter causing a temperature difference to occur when an electric current is flowing through the element, based on the Peltier effect. While one part of the Peltier element cools down, a different part thereof heats up. Such heat may again be removed by means of a heat exchanger or simply by providing the particular part generating the heat with an enlarged surface so that the heat is directly dissipated into the adjacent body part of the patient.

According to a third embodiment, the cooling device may be of a refrigerator-type construction. That is, heat exchanging pipes within a chamber to be cooled and heat exchanging pipes outside the chamber for dissipating the heat energy absorbed in the cooling chamber are provided along with a compressor for compressing the refrigerant gas when it exits the cooling chamber and an expansion valve for expanding the refrigerant gas before it re-enters the cooling chamber.

Turning now to the pump for advancing the infusion liquid from the reservoir to the infusion needle or needles, such pump may be a manually driven pump or an automatically driven pump. The manually driven pump may be formed from a balloon which may be manually compressed if suitably arranged under the patient's skin. The balloon type pump may at the same time serve as a reservoir for the infusion liquid, in particular for the saline solution. Preferably, however, an automatically driven pump is used. While the type of pump is not critical, one specific type of pump is particularly preferred. More particularly, an implantable pump preferably comprises a valve device having a first and a second valve member, each having a smooth surface facing each other so as to form a sealing contact between the first and second valve members and further having different liquid channels that can be brought into alignment by displacement of the two smooth surfaces relative to one another while maintaining the sealing contact. This type of pump is described in great detail in WO 2004/012806 A1. The first and second valve members are preferably made from a ceramic material for its excellent sealing capabilities over a long period of time and its inertness to many substances.

The pump may be a membrane type pump, as also described in WO 2004/012806 A1, but is not restricted to this type of pump. The membrane type pump may comprise a membrane displaceable by a piston as the piston moves, the piston being coupled to the valve device so as to slidably displace the first and second valve members relative to one another as the piston moves. Preferably, the pump will be implanted separate from the housing accommodating the needle or needles for remote implantation within the patient's body.

Due to the space constraints within the patient's body in the area where injection is to take place, it is advantageous to implant as many components of the system as possible remote from the housing accommodating the infusion needle or needles. In this context, the drive unit may comprise a mechanical drive element for transmitting kinetic energy from a remote location within the patient's body to the at least one infusion needle. The mechanical drive element may comprise a rotating shaft by which a considerable distance can be bridged within the patient's body. The rotating shaft may, upon rotation about its axis of rotation, cause movement of the infusion needle either directly or indirectly. More specifically, the rotating shaft may be in the form of a worm screw which, when turned, causes the infusion needle or needles to advance and retract and/or causes the infusion needle or needles to move laterally upon each advancement/retraction. Individual rotating shafts or worm screws may be provided for each individual infusion needle and/or for advancing and retracting the tip end of the infusion needle or needles on the one hand and laterally displacing the tip end of the infusion needle or needles on the other hand. Most preferably, the rotating shaft or worm screw is flexibly bendable, so that it can be freely arranged within the patient's body.

Alternatively or in addition, the drive unit may comprise at least one wire directly or indirectly cooperating with the infusion needle so as to cause movement of the infusion needle upon actuation of the wire. Thus, the wire may be pulled at one end thereof which is located within the patient's body remote from the injection sites. Preferably, the wire extends through the same conduit which connects the infusion needle or needles with the reservoir. More specifically, pulling the wire may cause the tip end of the infusion needle or needles to displace laterally from a first to a second of the different penetration areas or from a first penetration site to a second penetration site within a single one of the different penetration areas. A single pulling wire may be sufficient to cause movement of the infusion needle in one direction, whereas a spring element or any other pretensioning means may be provided to urge the infusion needle back to the initial starting position or to a different starting position. Alternatively, two pulling wires may be provided to move the infusion needle back and forth in a single dimension.

According to a preferred embodiment, the infusion needle is arranged for two-dimensional lateral displacement. This can be achieved by means of two pulling wires, preferably cooperating again with spring elements or other pretensioning means to provide a counterforce to be overcome by pulling the wires. Alternatively, three pulling wires may be provided to laterally displace the tip end of the infusion needle back and forth along at least two directions within a two-dimensional plane.

A pulling wire may also be arranged to advance or retract the infusion needle by pulling the wire. Again, a spring element or other pretensioning means may be provided to urge the infusion needle back to its initial starting position or to a different starting position.

Alternatively, the drive unit may comprise a hydraulic drive for transmitting hydraulic energy from a remote location within the patient's body to the at least one infusion needle for advancing the tip end thereof and/or for laterally displacing the tip end thereof. The infusion liquid itself may be used as the hydraulic medium providing the hydraulic energy, or a secondary liquid different from the infusion liquid may be used.

Further alternatively, the drive unit may comprise one or more electric motors inside the housing accommodating the at least one infusion needle. In this case, energy may be transmitted from a remote location within the patient's body to the at least one motor by means of appropriate wiring. Again, as in the two aforedescribed alternatives, a single motor may be provided for advancing and retracting the tip end of the infusion needle or needles and for laterally displacing the tip end of the infusion needle or needles, or individual motors may be provided for each individual infusion needle and/or for advancing the tip ends of the infusion needle or needles on the one hand and laterally displacing the infusion needle or needles on the other hand.

Even further alternatively, the drive unit may comprise an electromagnetic drive for laterally displacing and/or for advancing and retracting the tip end of the infusion needle or needles. For instance, the electromagnetic drive may comprise a group of electromagnets composed of a plurality of laterally spaced apart electromagnet first parts and at least one electromagnet second part, the electromagnet second part cooperating with an energized one of the electromagnet first parts. The electromagnet second part is fixedly connected to the infusion needle or needles either directly or indirectly so that upon energization of one or more of the electromagnet first parts the electromagnet second part and, thus, the infusion needle or needles will be caused to move. The arrangement of the electromagnet first parts and second part may be such that the electromagnet first parts are arranged in a first plane and the electromagnet second part is movable in front of or behind the first plane. Alternatively, the electromagnet first parts may face each other, thereby defining a first plane between them, and the electromagnet second part may be movable within the first plane. Depending on which one or ones of the electromagnet first parts are energized, the electromagnet second part with the infusion needle or needles fixed thereto will move accordingly. The electromagnet first parts preferably each include a magnetic coil.

In either one of the aforementioned alternatives, it is advantageous to transmit the driving energy through the conduit that connects the at least one infusion needle with the remotely implanted reservoir. That is, in the case of a mechanical drive element in the form of a wire or rotating shaft, the wire/shaft and the infusion liquid may be guided through a common conduit. The common conduit may comprise two separate paths, one for the shaft or wire and one for the infusion liquid. Such a common conduit facilitates the handling and arrangement of the system during implantation. Similarly, the wiring for transmitting electric energy to the motor or to the electromagnetic drive may be guided through a conduit connecting the infusion needle or needles with the reservoir.

Where the pump and/or drive unit is not actuated manually, a drive in the form of a motor may be arranged e.g. for electrically, magnetically or electromagnetically actuating the pump and/or drive unit or for hydraulically actuating the pump and/or drive unit. The motor is preferably arranged for actuating either the pump or the drive unit, thereby causing simultaneous actuation of the other, e.g. the drive unit or the'pump. A motor may also be provided for actuation of any other energy consuming part of the drug delivery device. More specifically, a plurality of motors may be provided, e.g. an individual motor for each infusion needle and/or an individual motor for displacing the tip end of the infusion needle in a lateral direction on the one hand and for advancing the tip end of the infusion needle through the housing's outer wall on the other hand.

Again, for reasons of space constraints in the area of implantation of the housing accommodating the infusion needle or needles, it is advantageous to remotely implant the motor within the patient's body separate from the housing. Again, actuating means may be provided for manual activation of the motor or motors, such actuating means preferably being adapted for subcutaneous implantation.

The term "motor" according to the present invention includes anything that employs energy other than manual power and either automatically transforms such energy into kinetic or hydraulic or another type of energy or directly uses such energy to activate the pump, drive unit and/or other part of the overall system. As such, it is possible that part of the drive unit also forms part of the motor, e.g. in the case of an electromagnetically actuated drive unit.

Coupling elements may be provided either for conductive or for wireless energy transfer from outside the patient's body to the motor. For instance, the motor may be arranged for being wirelessly driven by an external electromagnetic field.

An energy source for providing energy to at least one of the pump, the drive unit and the drive (motor) for driving the drive unit, and any other energy consuming part of the system may be provided. For instance, an external energy source for use outside the patient's body, such as a primary energy source or a battery, in particular a rechargeable battery, that may be mounted on the patient's skin, may be used to provide energy to the pump and/or drive unit and/or any other energy consuming part of the system. The energy source may in particular be connected to the at least one motor for actuating these components. An external energy source for wireless energy transfer may be adapted to create an external field, such as an electromagnetic field, magnetic field or electrical field, or create a wave signal, such as an electromagnetic wave or sound wave signal.

Where the energy is wirelessly transferred to the implanted components, a transforming device for transforming the wirelessly transferred energy into electric energy may be provided. Such transforming device is preferably adapted to be placed directly under the patient's skin so as to minimize the distance and the amount of tissue between the transforming device and the energy supply means outside the patient's body.

Instead of or in addition to an external energy source, the system may comprise an internal power supply for implantation within a patient's body. While such implantable power supply may be part of or may be contained within the housing accommodating the infusion needle or needles, it is preferred to provide the implantable energy source separate from the housing for remote implantation within the patient's body. Such implantable power supply preferably comprises energy storage means for long term storage of energy, such as a long-life battery or, more preferably, an accumulator. The accumulator has the advantage of being rechargeable. Preferably, the accumulator comprises a rechargeable battery and/or a capacitor.

Again, coupling elements for conductive or wireless energy transfer from an external power supply outside the patient's body to the accumulator may be provided for charging the accumulator from outside the patient's body when the device is implanted in the patient's body. Similarly, the accumulator may comprise coupling elements for conductive and/or wireless energy supply to the at least one motor of the drug delivery device.

A feedback subsystem, which may be part of a control unit described below, can advantageously be provided to send feedback information relating to the energy to be stored in the energy storage means from inside the human body to the outside thereof. The feedback information signal may be sent wirelessly. The feedback information is used for adjusting the amount of energy supply, in particular the amount of wireless energy transmitted by the energy transmitter. The feedback information preferably includes information on a parameter related to the charging process for controlling the charging process. It may specifically relate to an energy balance which is defined as the balance between an amount of wireless energy received inside the human body and an amount of energy consumed by the at least one energy consuming part. Alternatively, the parameter may relate to an energy balance which is defined as the balance between a rate of wireless energy received inside the human body and a rate of energy consumed by the at least one energy consuming part. The consumed energy preferably includes the energy that is consumed by the process of charging the implantable power supply.

Preferably, a control unit is provided for controlling an amount of infusion liquid to be administered through the at least one injection needle. A single command from the patient to the control unit, such as a single actuation of a press button or other type of switch, is sufficient for causing the control unit to control the injection of the drugs at two different locations within the patient's body. The control unit may be provided for controlling at least one of the pump, the drive unit and the motor and any other energy consuming part of the system and, where the system includes an internal or external energy source, said energy source. Again, the control unit is preferably separate from the housing accommodating the infusion needle or needles so as to be implantable within the patient's body. The control unit may be adjusted such that the appropriate amount of drugs will be administered at the appropriate time to the particular one of the injection sites. Automatic administration will substantially relieve the patient.

Preferably, the control unit has a data transfer port for data transfer between an external data processing device outside the patient's body and the control unit implanted in the patient's body, regardless of whether the control unit is contained in the housing accommodating the infusion needle or needles or whether it is implanted within the patient's body remote from said housing. The data transfer port allows for monitoring the control unit to adapt the system to changing needs of the patient. Preferably, the data transfer port is a wireless transfer port for the data transfer, so as to provide easy data exchange between the control unit and the external data processing device, e.g. during a visit to the doctor. Most preferably, the control unit is programmable to further increase its adaption flexibility. Instead of or in addition to the external data processing device, the control unit may comprise an external component for manual operation by the patient for setting into operation the control unit.

Apart from or as a part of the control unit, feedback may be provided on parameters relevant for the treatment. Such parameters may be either physical parameters of the patient and/or process parameters of the system. For this purpose, at least one feedback sensor is provided for detecting such parameters. For instance, the feedback sensor may be adapted to detect one or more parameters relating to any of the following: drug level, flow volume in blood vessel, pressure, electrical parameters, distension, distance, etc.

The feedback sensors may be connected to the control unit and the control unit may comprise a control program for controlling drug delivery in response to one or more signals from the feedback sensors. In addition or alternatively, feedback data may be transferred from the control unit to the external data processing device. Such feedback data may be useful for the doctor's diagnosis.

The penetration areas of the wall or walls of the housing or housings within which the infusion needle or needles are disposed may be arranged in the patient's body at various locations. For instance, they may be arranged adjacent the left and right corpora cavernosa and/or the two deep arteries running through the left and right corpora cavernosa and/or muscle tissue regulating blood flow through the patient's left and right corpora cavernosa and/or another kind of tissue in close proximity to the left and right corpora cavernosa.

A holder may be used to secure the corpora cavernosa to the housing or housings so that the housing rests in place.

Other components of the system are preferably remotely implanted, such as adjacent the patient's symphyseal bone. As discussed above, some components of the system may be implanted subcutaneously. Subcutaneous implantation increases the possibilities of wireless energy and/or data transfer between the implanted and the extracorporal parts of the system. Also, refilling the reservoir through an injection port by means of a replenishing needle penetrating through the patient's skin is substantially facilitated when an injection port of the reservoir is implanted subcutaneously. In particular, the compartment of the reservoir containing the saline solution might need to be refilled frequently, whereas the other compartments comprising individual small doses of the drug would need no refill. It should be understood, however, that depending upon the circumstances any implantable component of the system may be placed in the abdomen or even in the thorax. Activating means for direct manual operation by the patient may also be provided to be implanted subcutaneously, e.g. for setting into operation one or more of the aforementioned motors or for simply setting into operation the control unit of the system. Such activating means may be in the form of a subcutaneously implantable switch manually operable by the patient from outside the patient's body.

The various aforementioned features of the invention may be combined in any way if such combination is not clearly contradictory. The invention will now be described in more detail in respect of preferred embodiments and with reference to the accompanying drawings. Again, individual features of the various embodiments may be combined or exchanged unless such combination or exchange is clearly contradictory to the overall function of the device. In particular, while most of the embodiments described hereinafter relate to systems having one or more infusion needles entirely accommodated within one or more housings, it is likewise possible in all of these embodiments to employ long, flexibly bendable needles having only the front ends thereof accommodated in said housing or housings and having the respective rear ends disposed in one or more second housings remotely implanted within the patient's body.

BRIEF DESCRIPTION OF THE DRAWINGS

FIG. 6 shows a plan view of a part of the drug delivery device of FIGS. 4 and 5, FIG. 7 shows a cross-sectional view of a penetration membrane made from a composite material.

DETAILED DESCRIPTION OF THE DRAWINGS

Figure 1:
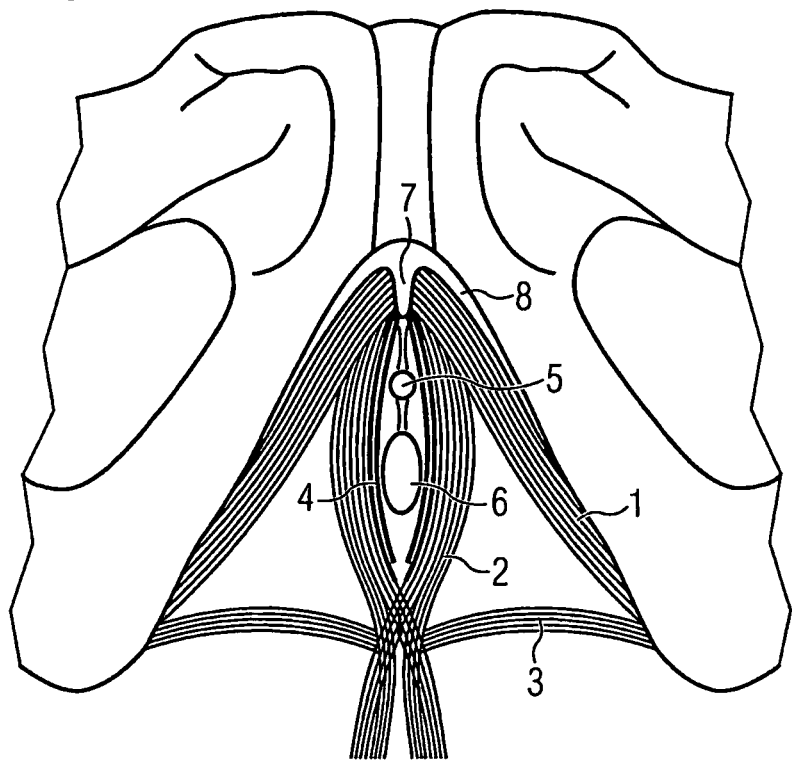
FIG. 1 shows the muscles of the female's perineum.

FIG. 1 shows the muscles of the perineum of a female. Reference numerals 1, 2 and 3 designate the ischiocavernosus muscles, bulbospongiosus muscles and superficial transverse perineal muscles, respectively. The labia minora 4, of which only a lower section is visible in the dissection shown in FIG. 1, surround the vestibule into which both the external urethral and the vaginal orifices 5, 6 open. The clitoris 7 is located where the labia minora 4 meet anteriorly. In many details, the clitoris 7 resembles the structure of the penis, of which it is homolog, although it is of reduced scale and has no association with the urethra. That is, the clitoris consists of a root and a body, which are composed of two crura 8, two corpora cavernosa and the glans, which is the most sensitive part of the clitoris and is usually covered by a prepuce formed from the labia minora 4. The ischiocavernosus 1 embraces the crus 8 of the clitoris, inserting onto the inferior and medial aspects of the crus 8 and to the perineal membrane medial to the crus.

The bulbospongiosus muscle 1 assists the erection by compressing outflow via the deep perineal vein and by pushing blood from the bulb into the body of the clitoris. The bulbospongiosus muscle 2 on each side of the vagina encloses the bulb of the bulb of the vestibule and the greater vestibular gland, which are not visible in this dissection. The ischiocavernosus muscle 1 maintains erection of the clitoris by compressing outflow veins and pushing blood from the root of the clitoris into the body of the clitoris.

Figure 2:
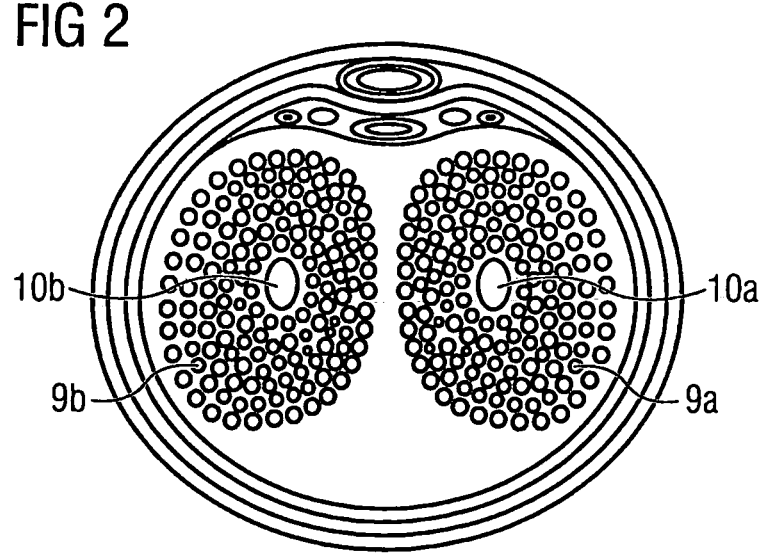
FIG. 2 shows a cross-section through the clitoris.

FIG. 2 is a cross-sectional schematic view through the clitoris. As can be seen, the clitoris is composed of two cylindrical bodies of erectile cavernous tissue: the paired corpora cavernosa 9a, 9b and the deep arteries 10a, 10b running near the center of the corpora cavernosa 9a, 9b, supplying the erectile tissue in these structures. The deep arteries 10a, 10b of the clitoris 7 are the main vessels of the cavernous spaces in the erectile tissue of the corpora cavernosa 9a, 9b and are therefore involved in the erection of the clitoris. They give off numerous branches that open directly into the cavernous spaces. When the clitoris is flaccid, these arteries are coiled, restricting blood flow.

Figure 3:
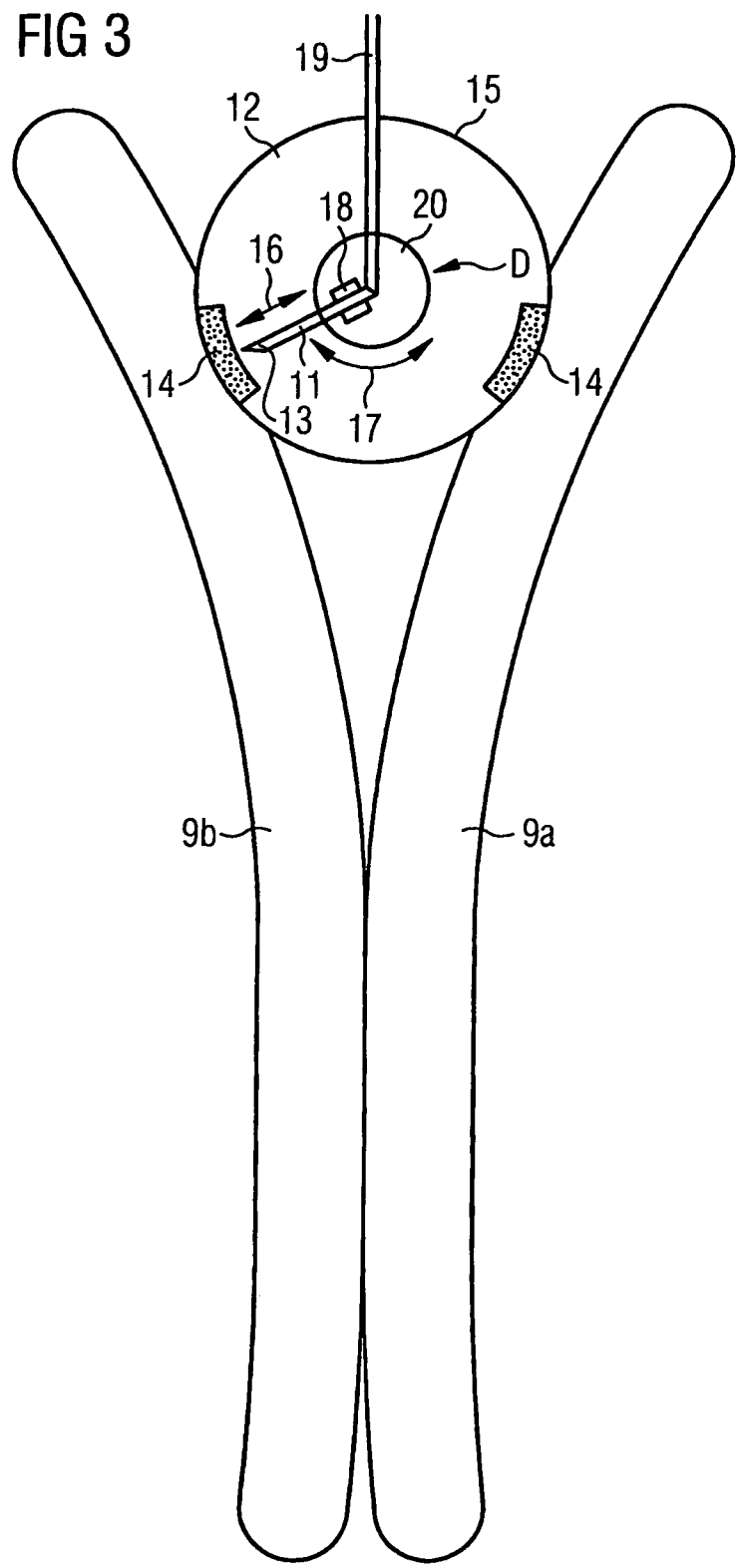
FIG. 3 shows a top view of a first embodiment of the invention including a single needle.

For reasons of simplification, the following figures only display the corpora cavernosa 9a, 9b very schematically and not true to scale. FIG. 3 shows a top view on a part of the system according to a first embodiment. More specifically, a single infusion needle 11 is arranged in a housing 12 with a tip end 13 of the needle 11 being positioned such that it can be advanced and retracted through a self-sealing window area 14 in the housing's 12 outer wall 15 in a longitudinal direction 16, so as to pierce the corpus cavernosum 9a or 9b located adjacent the window area 14.

Two window areas 14 are provided in the outer wall 15 of the housing 12, one adjacent each of the two corpora cavernosa 9a, 9b. The infusion needle is displaceable in a lateral direction 17 between the two window areas 14 by means of a drive unit D. The same drive unit D or a different drive unit may cause the infusion needle 11 to be advanced and retracted. For this purpose, the infusion needle 11 is mounted on a slide 18 for longitudinal advancement and retraction. A conduit 19 is connected to one end of the infusion needle 11 to supply infusion liquid through the infusion needle 11 to the tip end 13 thereof.

In operation, the infusion needle 11 will first be advanced with the tip end 13 thereof to penetrate one of the two self-sealing penetration windows 14, injection fluid containing a drug for stimulation of clitoris erection will be injected into the corpus cavernosum 9b through the infusion needle 11 and, thereafter, the infusion needle 11 will be retracted again. Upon retraction of the infusion needle, the infusion needle will be laterally displaced along the direction 17 so that the tip end 13 thereof comes to lie in front of the other of the two self-sealing window areas 14, the infusion needle 11 will be advanced again so that infusion liquid can be injected through the tip end 13 thereof into the other corpus cavernosum 9b and then the infusion needle 11 will be retracted again. At the end of this procedure, the infusion needle 11 will return to its initial position shown in FIG. 3.

The structure of the system shown in FIG. 3 may be purely mechanical. For instance, as will be described in more detail below, the pressure with which the infusion liquid is advanced through the conduit 19 towards the needle 11 may in cooperation with spring elements cause the needle 11 to be advanced, retracted and laterally displaced to the other window area 14. Thus, after two pulses of injection fluid advanced through the conduit 19 towards the needle 11, the needle 11 will automatically return to its starting position shown in FIG. 3.

Figure 4:
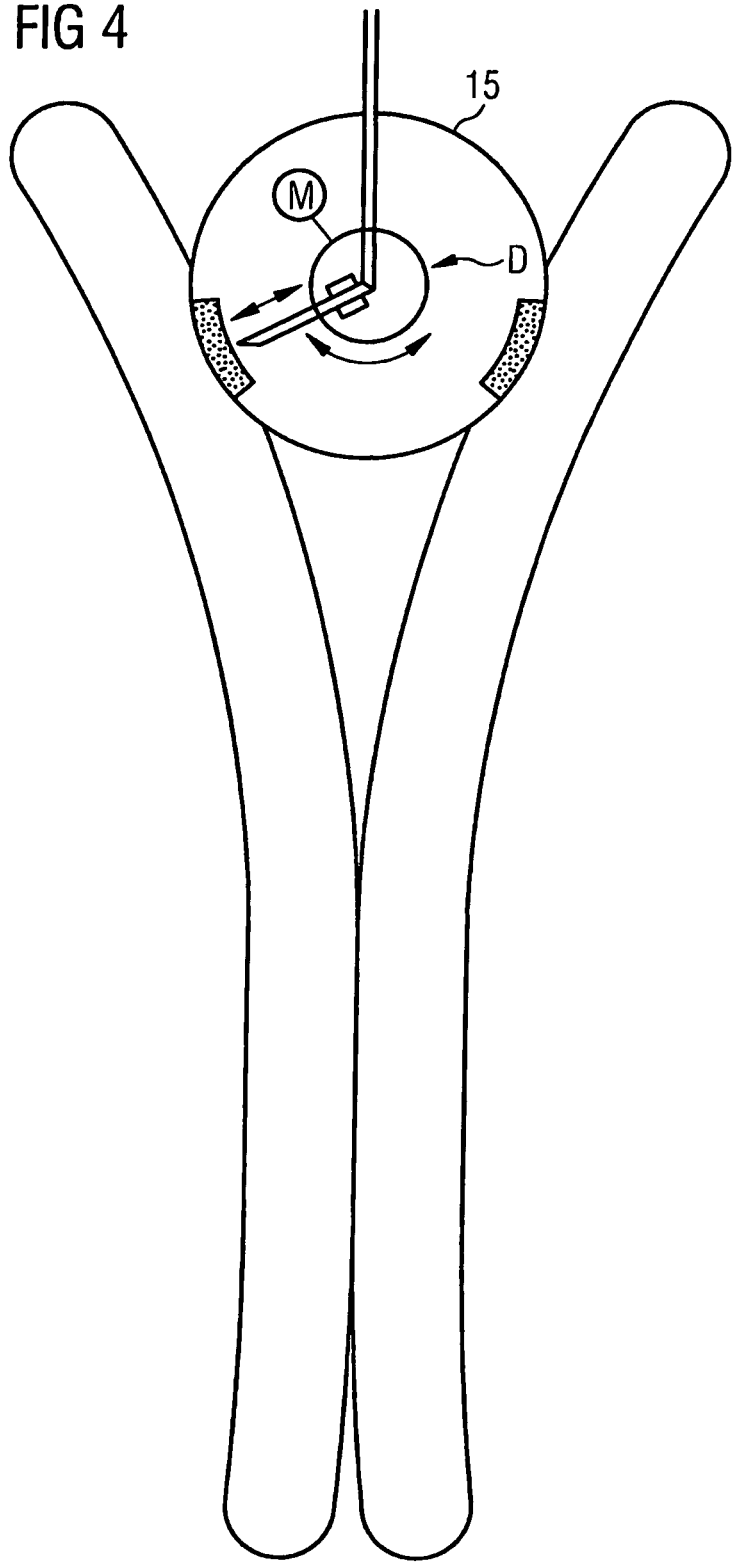
FIG. 4 shows a top view of a second embodiment of the invention including a single needle and a motor accommodated in a common housing.

However, it is likewise possible to incorporate a motor M or a plurality of motors M within the housing 15 in order to achieve the desired needle displacement by means of the drive unit D. This is schematically shown in FIG. 4. Of course, the motor M will have to be provided with energy and will need to be controlled in an appropriate manner so as to obtain the desired effect. This is not specifically shown in FIG. 4. The energy is preferably transmitted to the motor M from an energy source either remotely implanted inside the patient's body or provided externally of the patient's body.

The drive D may be configured such that after each penetration cycle (consisting of two injections) the infusion needle 11 stops at a position different from the starting position so that the tip end 13 thereof penetrates the window areas 14 in the next following injection cycle at different sites as compared to the foregoing injection cycle.

Figure 5:
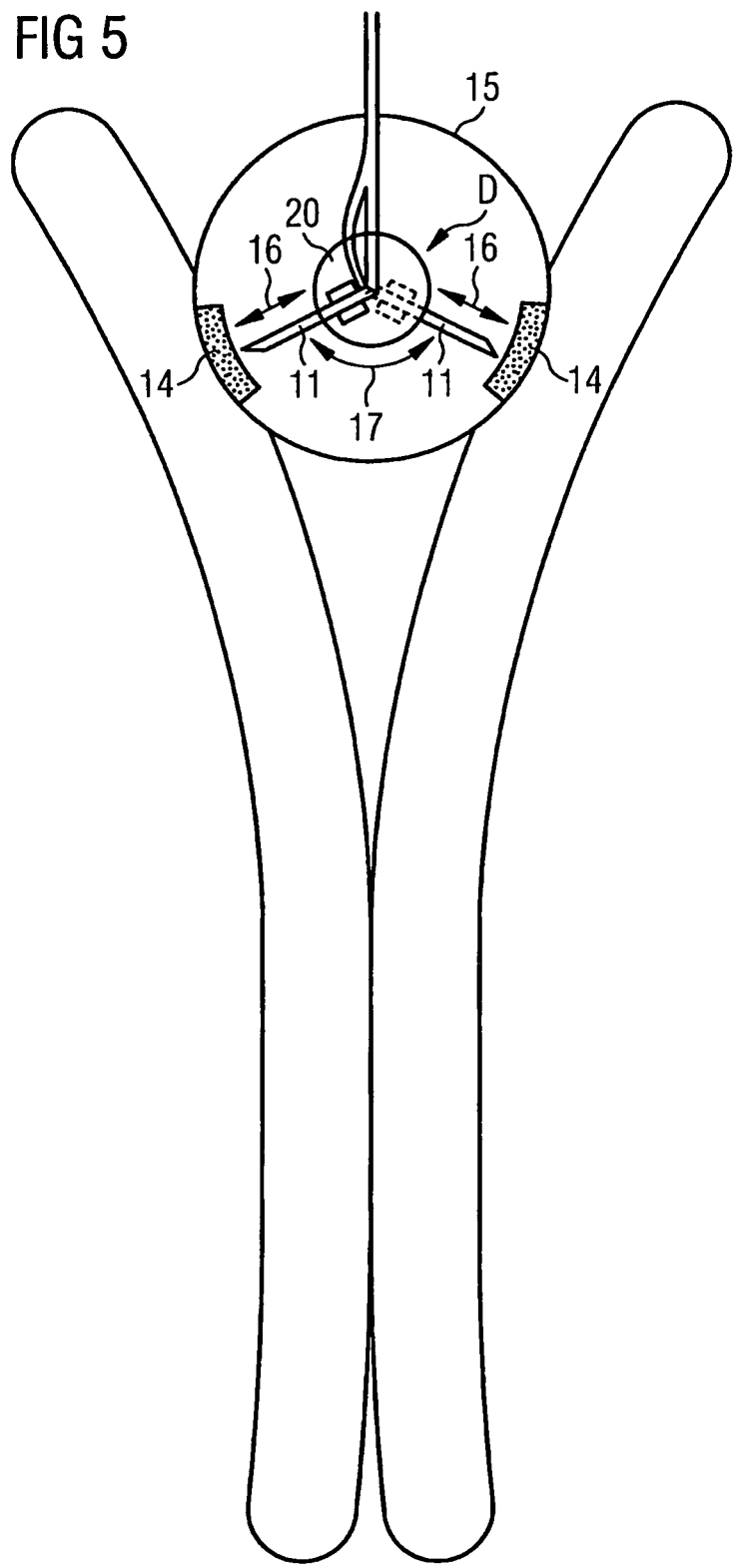
FIG. 5 shows a top view of a third embodiment of the invention including two needles in a common housing.

FIG. 5 shows a top view on a third embodiment which differs from the first and second embodiments in that it comprises two infusion needles 11 contained in the housing 15. Thus, when infusion liquid is guided through the conduit 19 towards the two infusion needles 11, both needles are advanced and retracted simultaneously along the direction 16, so that injection of infusion liquid occurs at exactly the same time. The drive unit D or a separate drive unit may be used to turn the turntable 20 on which the infusion needles 11 are mounted, stepwise in the direction 17 so that the window areas 14 will be penetrated by the tip end of the infusion needle 11 at different penetration sites during the next following injection cycle. Again, one or more motors M, not shown in FIG. 5, may be used for driving one or more of the components of the drive unit D.

The principle of a guide structure for laterally displacing the infusion needle will now be described in context with FIG. 6. Such guide structure may be used e.g. for each of the two infusion needles 11 shown in FIG. 5 or may also be used slightly modified for the lateral displacement of the infusion needle 11 shown in FIGS. 3 and 4.

The guide structure 28 is securely fixed adjacent the self-sealing window area 14 which itself is implanted adjacent the patient's corpus cavernosum 9b. The guide structure 28 comprises a guide pin 27 securely connected to the infusion needle 11 (not shown) such that the infusion needle 11 cooperates with the guide structure 28. Upon advancement or retraction of the infusion needle 11, the guide pin 27 will be guided in the guide structure 28 and thereby laterally displace the infusion needle 11, which lateral displacement causes rotation of the turntable 20 (not shown in FIG. 6). Resilient flaps 28a, 28b within the guide structure 28 serve to guide the guide pin 27 through the entire guide structure 28 upon repeated advancement and retraction of the infusion needle 11. The guide structure 28 is designed to provide different penetration sites through the self-sealing window area 14 into the corpus cavernosum 9b. Where it is desired, the trajectory of guide structure 28 may include a return path 28c for the guide pin 27 to return to its starting position shown in FIG. 6. Such return action will be caused by a return spring 29 which is permanently fixed to a rigid part of the housing 15.

The same structure can likewise be used in the embodiments shown in FIGS. 3 and 4 to displace the single infusion needle 11 laterally between the two window areas 14. Of course, the structure would have to be slightly adapted to accommodate for the larger distance to be overcome between the two window areas 14.

FIG. 7 shows a preferred embodiment of a penetration membrane to be used as the self-sealing window area 14 in the outer wall 15 of the housing 12. The penetration membrane 30 is made from a composite material. The same material can also be used for other flexible wall portions or for an infusion port that will be described below in connection with another embodiment. The composite material of penetration membrane 30 shown in FIG. 7 comprises an outer shape-giving layer 30a defining a volume in which a self-sealing soft material 30b is contained. Self-sealing soft material 30b can be of gel type having a viscosity such that it does not flow through any penetrations caused by the infusion needle 11 during penetration of the outer shape-giving layer 30a. Instead of a single outer shape-giving layer 30a, the shape-giving layer 30a may comprise a plurality of layers. The outer shape-giving layer 30a preferably comprises silicone and/or polyurethane, since such materials can be produced to have self-sealing properties in respect of penetrations resulting from the infusion needle 11.

Figure 8:
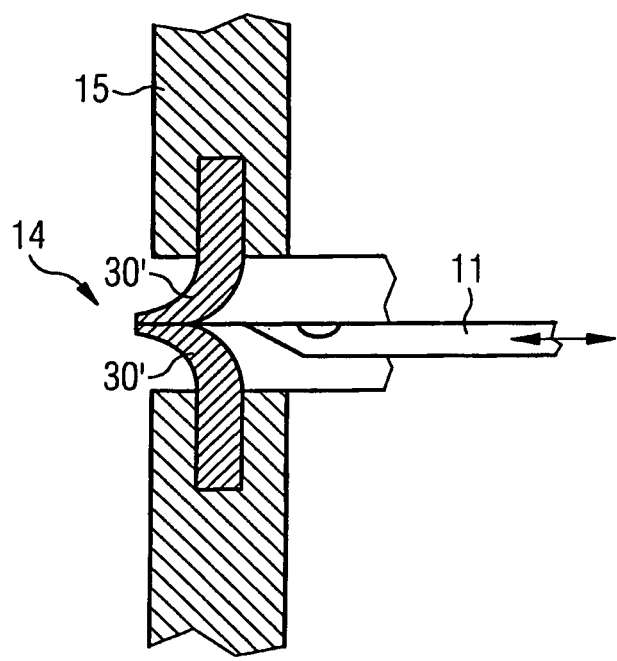
FIG. 8 shows a cross-sectional view through the outer wall with flaps in the penetration area.

Instead of a self-sealing membrane, the window area 14 in the outer wall 15 of the housing 12 may be formed by one or more flaps, as shown in FIG. 8. Two flaps 30' being made from a resilient, biocompatible material are arranged so as to form a slit which is normally closed and through which the infusion needle 11 can pass when it is advanced. Upon advancement of the infusion needle 11, the needle will push aside the normally closed flaps 30', and when the needle 11 is retracted again, the flaps 30' will return to their normally closed position so as to form a seal against ingression of body liquid.

Figure 9:
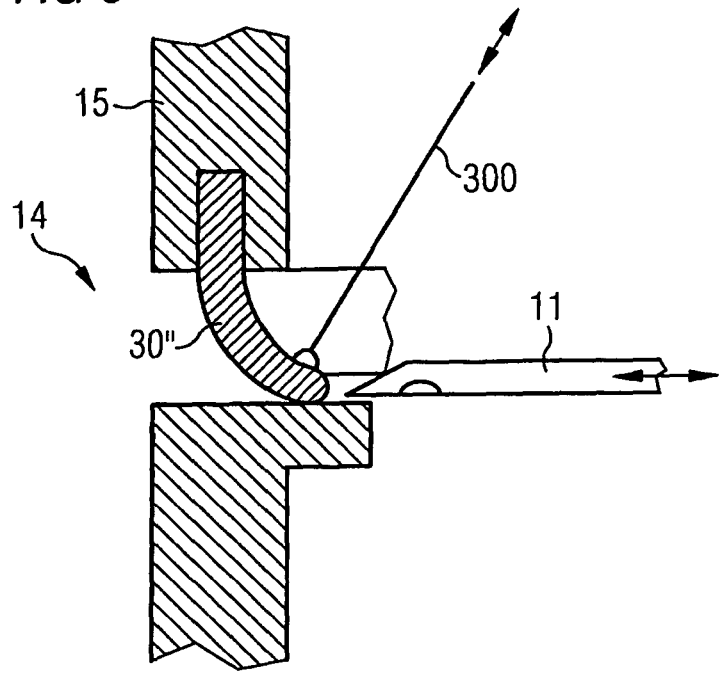
FIG. 9 shows a cross-sectional view through the outer wall with an actively openable door in the penetration area.
Figure 10:
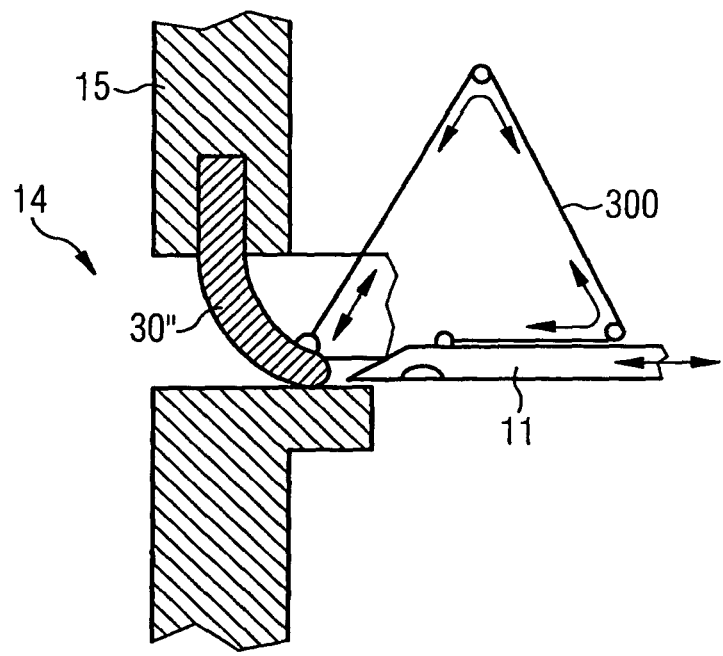
FIG. 10 shows a cross-sectional view through the outer wall with an actively openable door according to another embodiment.

FIG. 9 shows a different embodiment. In this case, the self-sealing window 14 in the outer wall 15 comprises a door 30" which can be opened by mechanical action. In the embodiment shown, the door is formed by a flap made from a resilient, biocompatible material which keeps the window area 14 closed in its normal position. A pull wire 300 is attached to one end of the door 30" in order to allow for opening the door by pulling the pull wire 300. The pull wire 300 or any other drive connected to the door 30" forms part of the drive unit coupled to the infusion needle 11. For instance, as is shown in FIG. 10, the pull wire 300 may be attached directly to the infusion needle 11 so that advancement of the infusion needle 11 will simultaneously cause the door 30" to be lifted up so that the infusion needle 11 can pass underneath the door 30" and thus penetrate the outer wall 15 easily. Due to the resiliency of the door material, the door 30" will automatically close when the force, such as the pulling force exerted via the pull wire 300, is released. Instead or in addition, the closing action may be supported by at least one spring element urging the door into its closed position.

Figure 11:
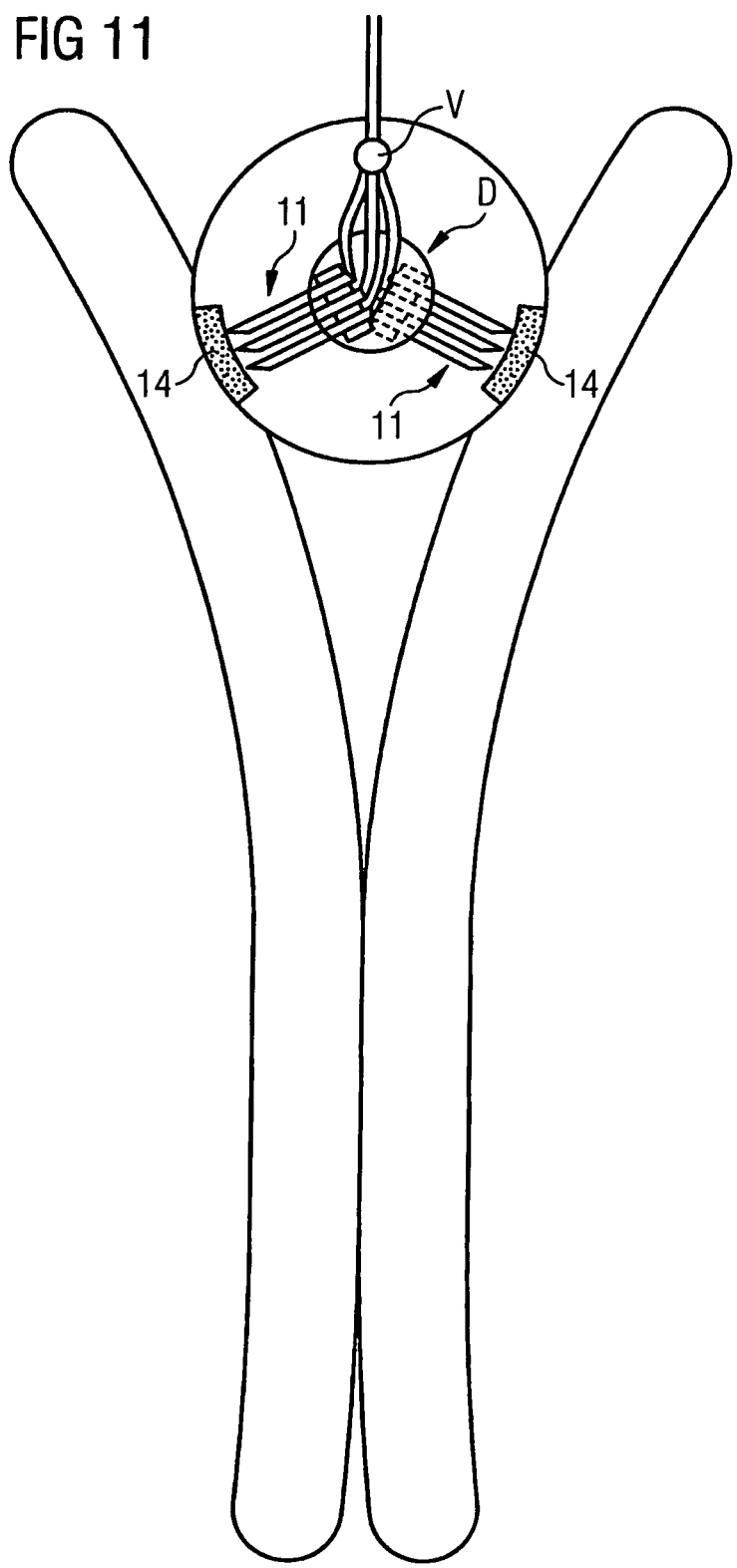
FIG. 11 shows a fourth embodiment including a plurality of needles within a common housing.

FIG. 11 shows a fourth embodiment comprising a plurality of infusion needles for each of the two window areas 14. In this embodiment it is not necessary to provide a turntable by which the needles can be pivoted stepwise in order to laterally displace the needles from one penetration site to a different penetration site within the same window area 14. Instead, upon successive injection cycles a different one of the plurality of injection needles will be advanced and retracted for each of the two window areas 14. Thus, the effect achieved is the same as in the embodiment shown in FIG. 5. However, instead of the turntable 20 (FIG. 5) a valve V is needed to direct the infusion liquid to only one of the plurality of infusion needles 11 in each of the two window areas 14. More specifically, depending upon the position of the valve V, a first one of the infusion needles 11 in the first window area 14 and a first one of the plurality of the infusion needles 11 in the second window area 14 will be advanced and retracted simultaneously, and during the next following infusion cycle, another one of the plurality of infusion needles will be advanced and retracted in the two window areas 14.

Figure 12:
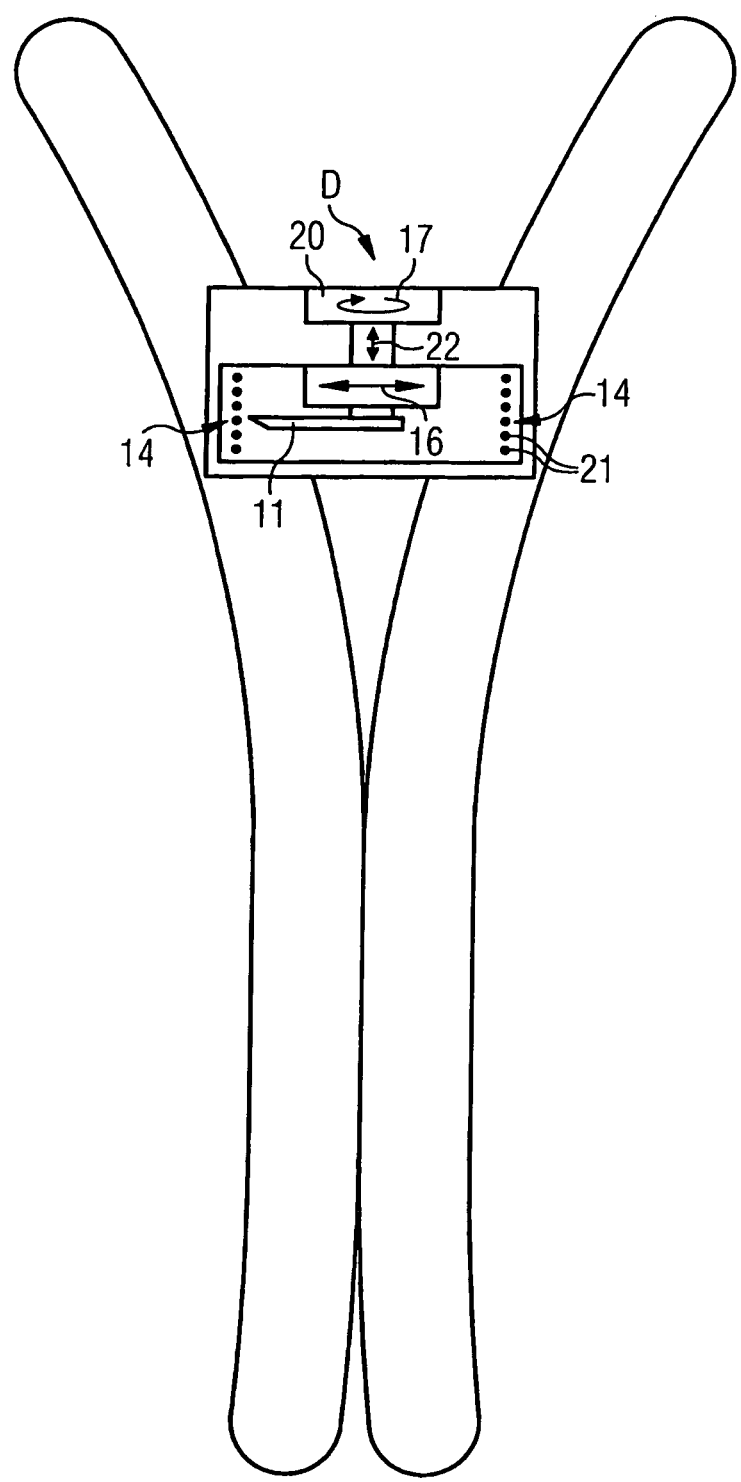
FIG. 12 shows a side view of a fifth embodiment of the invention comprising a single needle which is laterally and vertically displaceable.

FIG. 12 shows a side view of a fifth embodiment which differs from the first and second embodiments shown in FIGS. 3 and 4 in that the single infusion needle 11 is not only laterally displaceable in the direction 17 between the two window areas 14 but also laterally displaceable between different penetration sites 21 within the same penetration area 14. More specifically, the direction of lateral displacement of the tip end of the infusion needle 11 within each of said different penetration areas 14 is perpendicular to the direction of lateral displacement between the different penetration areas 14. To achieve this result, the drive unit D is configured to longitudinally advance and retract the infusion needle 11 along a direction 16, to pivot the infusion needle 11 by means of a turntable 20 between the two penetration areas 14 along a pivoting direction 17 and to raise or lower the infusion needle 11 along a third direction 22 perpendicular to the longitudinal direction 16. A suitable purely mechanical construction may perform this function. However, one or more motors may also be provided to perform one and/or the other of these functions.

Figure 13:
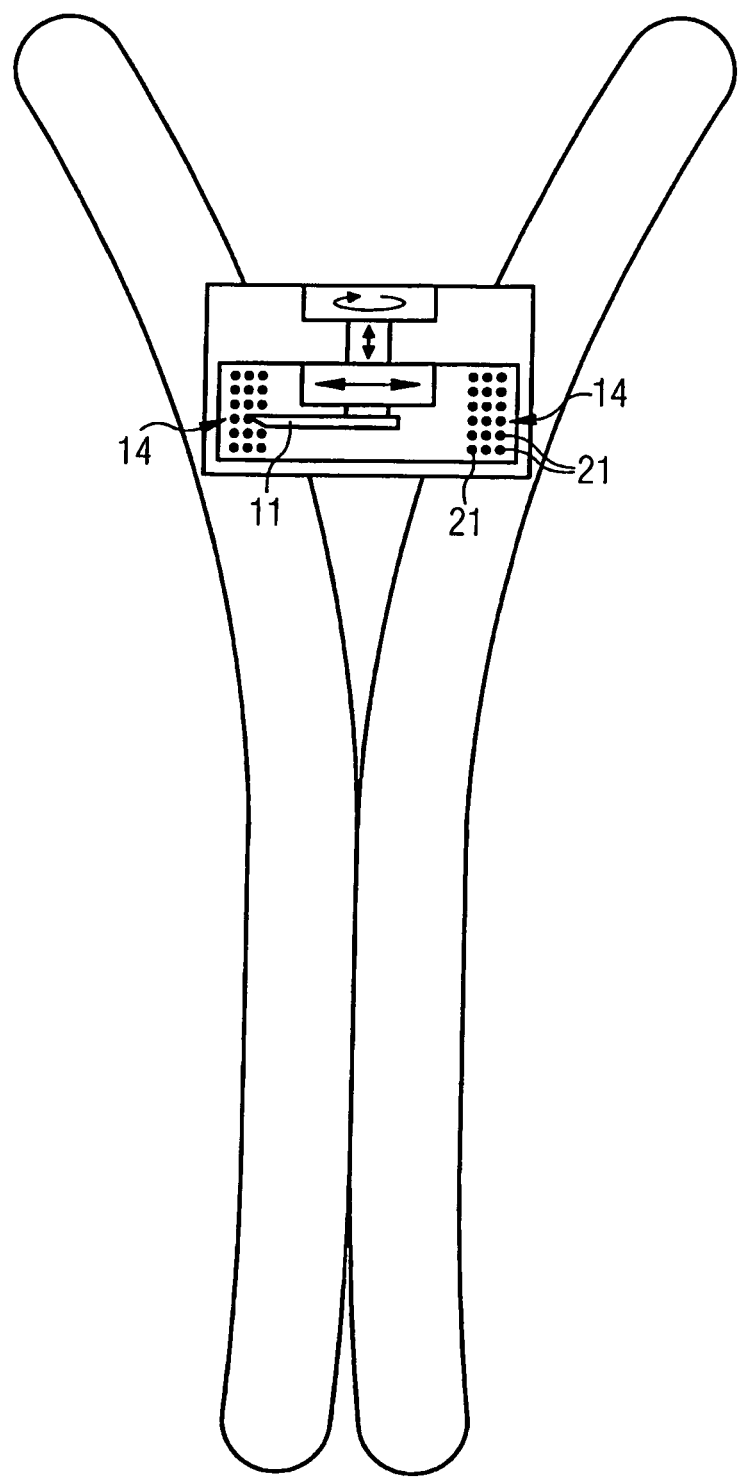
FIG. 13 shows a side view of a sixth embodiment of the invention similar to the fifth embodiment, but with more steps for laterally displacing the needle.

FIG. 13 shows a side view of a sixth embodiment similar to the fifth embodiment shown in FIG. 12. In contrast to FIG. 12, the infusion needle 11 is not only laterally displaceable between different penetration sites 21 within the same penetration area 14 in a direction perpendicular to the direction of lateral displacement between the two penetration areas 14, but is also laterally displaceable within the same penetration area 14 in a direction parallel to the direction of lateral displacement between the different penetration areas 14. In other words, the tip end of the infusion needle 11 is laterally displaceable in two dimensions within the same penetration area 14.

Figure 14:
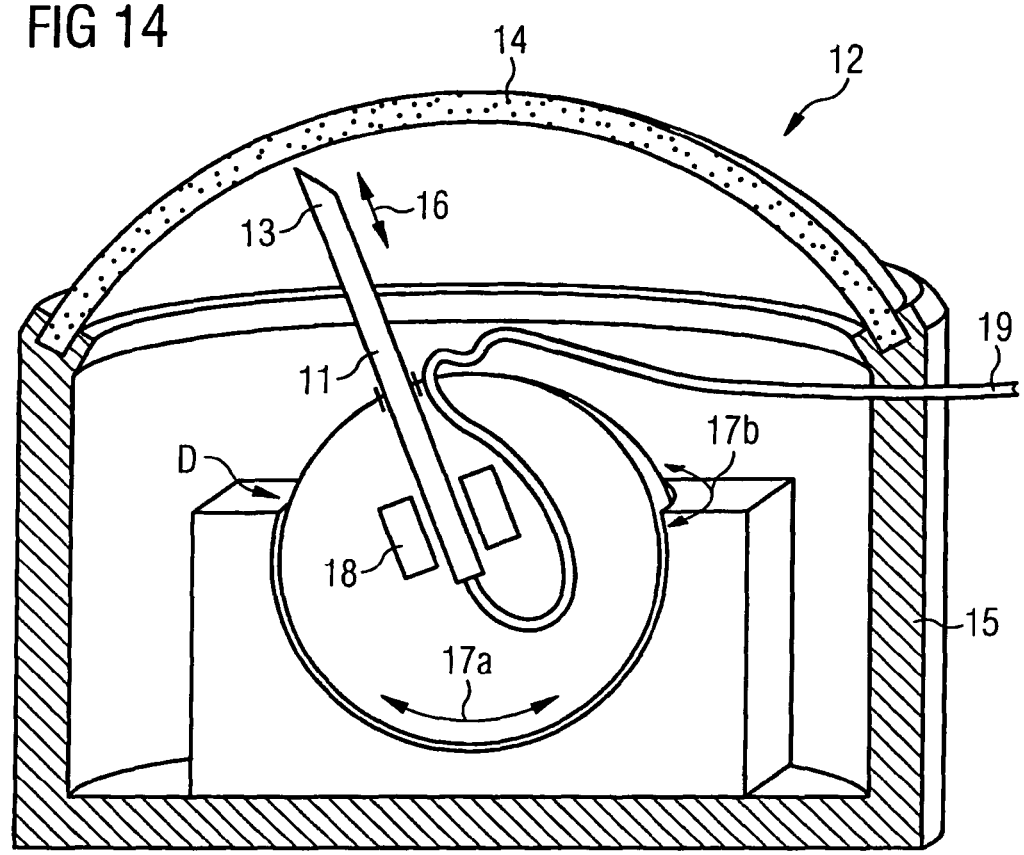
FIG. 14 shows a seventh, spherical embodiment of the invention for obtaining a three-dimensional array of penetration sites.

FIG. 14 shows a seventh embodiment which enables the infusion needle 11 to be moved along a three-dimensional, spherically curved array of penetration sites. In this embodiment, a part of the housing 12, more specifically the window area 14, is spherically curved and the needle 11 is mounted in a sphere so that upon rotation of the sphere along the directions 17a and 17b the tip end 13 of the needle 11 can be moved to any position in front of the window area 14. Once an appropriate position has been adjusted for the tip end 13, the needle 11 can be advanced on the slide 18 so as to penetrate the window area 14. Instead of accommodating the slide inside the sphere, it may likewise be mounted on the outer surface of the sphere. Similarly, the infusion needle 11 itself can be mounted on the outer surface of the sphere. The mechanism for moving the sphere along the directions 17a, 17b can be of many different types, such as mechanical by means of rollers or magnetic.

Figure 15:
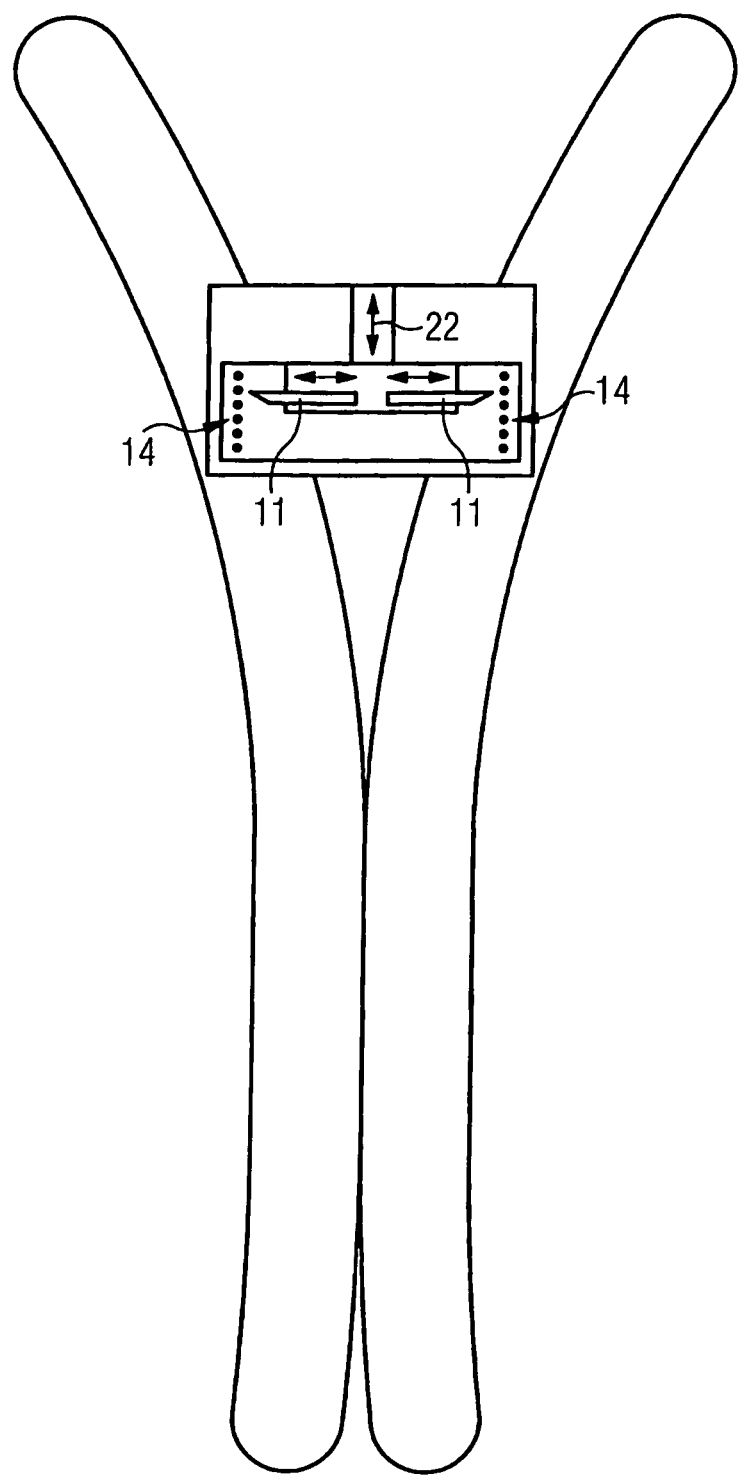
FIG. 15 shows a side view of an eighth embodiment of the invention comprising two needles in a common housing which are laterally and vertically displaceable.
Figure 16:
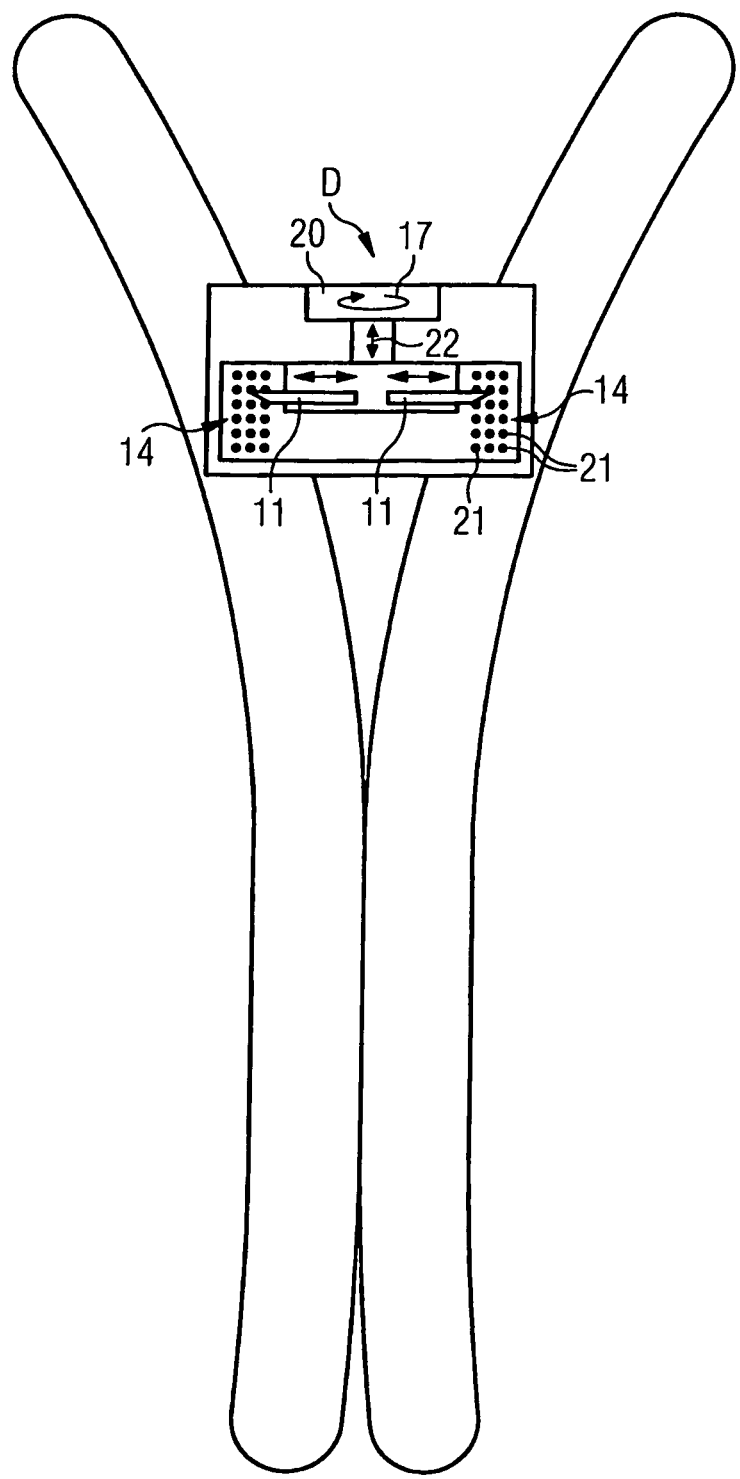
FIG. 16 shows a side view of a ninth embodiment of the invention comprising two needles similar to the eighth embodiment, but with more steps for laterally displacing the needle.

FIG. 15 shows a side view of an eighth embodiment similar to the third embodiment shown in FIG. 5. That is, two needles 11 are provided in a common housing so as to be longitudinally movable in order to advance and retract the tip ends thereof through the penetration areas 14. The infusion needles 11 is mounted on a turntable 20, as in the third embodiment of FIG. 5, so as to change the injection sites 22 within a penetration area 14 upon each injection cycle. In addition, the two injection needles can be raised and lowered along a direction 22, similar to the fifth embodiment described above in relation to FIG. 12. Again, the result is that the direction of lateral displacement of the tip ends of the two infusion needles 11 within each of the two different penetration areas 14 is perpendicular to the direction of distance between the two different penetration areas 14. Of course, this embodiment, like the sixth embodiment shown in FIG. 13, can also be modified such that the tip ends of the two infusion needles 11 are laterally displaceable in two dimensions within the same penetration area 14. This is shown in FIG. 16, displaying a side view of a ninth embodiment. In this embodiment, like in the sixth embodiment shown in FIG. 13, the tip ends of the two infusion needles 11 are laterally displaceable in two dimensions within the same penetration area 14.

Figure 17:
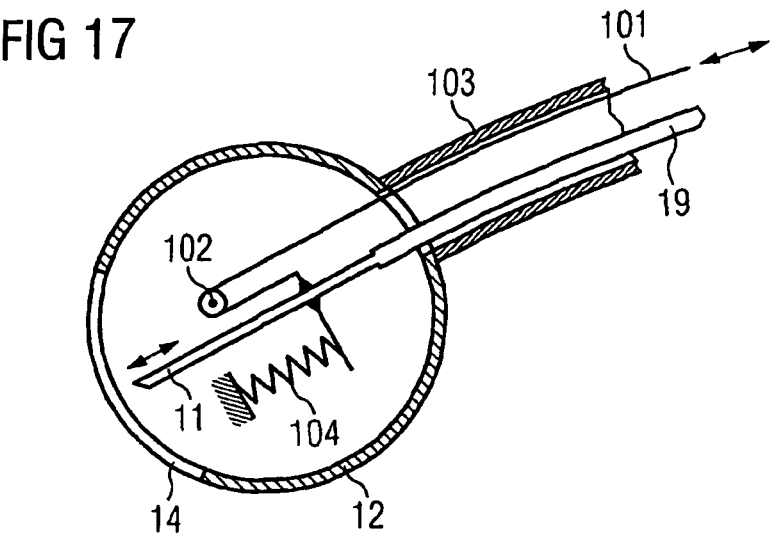
FIG. 17 shows a tenth embodiment with a principle of advancing and retracting an infusion needle by means of a pull wire.

FIG. 17 shows a tenth embodiment with a principle of advancing and retracting the infusion needle 11 by means of a pull wire 101. The pull wire 101 is redirected about a pin 102 such that by pulling the wire 101 at an end remotely located somewhere in the patient's body the tip end of the infusion needle 11 will be advanced through the window of the housing 12. A helical spring provides a counterforce so that the infusion needle 11 will be retracted once the pulling force on the pull wire 101 is released. This principle can be combined with other embodiments described hereinbefore and hereinafter. Instead of the helical spring 104, a second pull wire may be provided to retract the infusion needle 11. It is even possible to use a single pull wire 101 running around two pins 102 in a loop, so that pulling the wire 101 in the one direction or in the other direction will cause advancement or retraction of the infusion needle 11.

The pull wire 101 and the conduit 19 for the infusion liquid are guided in a common sheath 103. The common sheath 103 has various functions. First, it gives support to the pull wire 101 in bending sections. Second, it facilitates implantation of the conduit 19 along with the pull wire 101. Third, it protects the pull wire 101 against any build-up of fibrosis. In the case that the infusion needle 11 is long and flexibly bendable, the pull wire 101 and the long infusion needle may be guided in the common sheath 103.

Figure 18:
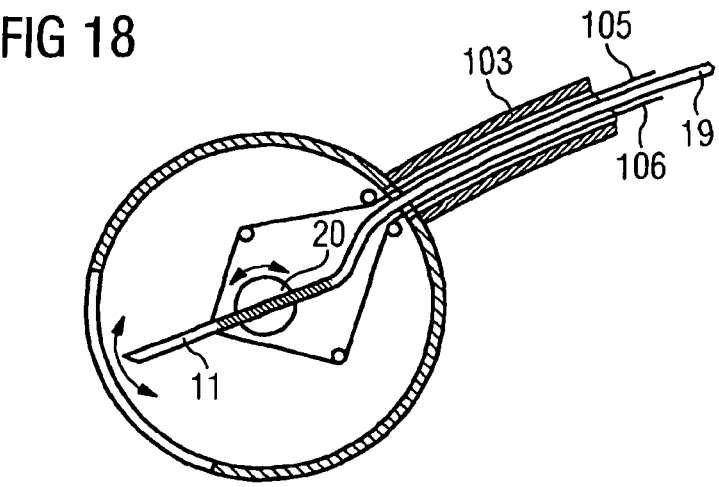
FIG. 18 shows an eleventh embodiment with a principle of laterally displacing an infusion needle by means of pull wires.

FIG. 18 shows an eleventh embodiment which involves remotely actuated pull wires 105, 106 guided within a common sheath 103 along with the conduit 19 for the infusion liquid. The pull wires 105 and 106 are directly attached to the infusion needle 11 on opposite sides thereof so that the infusion needle 11 which is mounted on a turntable 20 will be laterally displaced in the one direction or in the other direction depending on whether the wire 105 or the wire 106 is pulled. Instead of using two wires 105, 106, one of the wires may be replaced with a pretensioning means, such as the helical spring 104 in FIG. 17. In addition, a further wire, in particular third wire (not shown), may be provided for lateral displacement of the infusion needle 11 in a further direction, so that a two-dimensional lateral displacement can be achieved by pulling the appropriate wires.

The pull wires may alternatively be attached to an element other than the infusion needle 11, provided that the infusion needle 11 is connected to such other element, so that when the other element is moved or turned by pulling one or more of the wires the tip end of the infusion needle 11 will be displaced accordingly.

In the case that a long, flexibly bendable needle is provided with the tip end thereof being arranged in a first housing for penetrating the outer wall of the first housing and the other end is arranged in a remotely implanted second housing, one can dispense with the turntable 20 and achieve accurate lateral displacement of the tip end of the needle by pulling the appropriate one of three pull wires which are attached either directly or indirectly to the circumference of the front end of the infusion needle at regularly spaced intervals.

Figure 19:
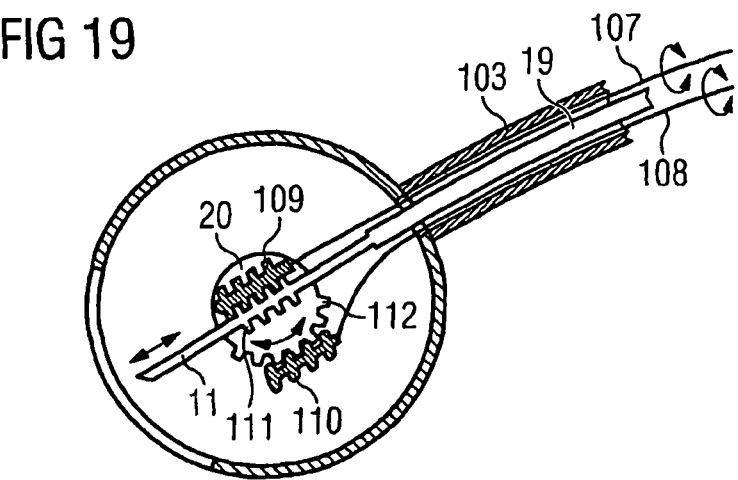
FIG. 19 shows a twelfth embodiment with a principle of advancing and retracting a needle and laterally displacing a needle by means of rotating shafts.

FIG. 19 shows a twelfth embodiment with a different principle of advancing and retracting the tip end of the infusion needle, on the one hand, and laterally displacing the tip end of the infusion needle 11, on the other hand. Instead of pull wires, rotating shafts 107, 108 are provided. The drive for driving the rotating shafts 107, 108 is remotely located somewhere in the patient's body. The front ends of the rotating shafts have a threading 109, 110, e.g. in the form of a worm screw, meshing with the teeth of a rack 111, 112 formed either directly or indirectly on the infusion needle 11 and on the turntable 20, respectively. Thus, by turning the rotating shaft 107, the infusion needle 11 will advance or retract, as the case may be, due to the cooperation of the worm screw 109 and the rack 111. The gearing 109, 111 may likewise be arranged remote from the first housing, i.e. within the second housing accommodating the respective other end of the needle (which is particularly suitable when a long, flexibly bendable needle is used—not shown). Similarly, by turning the rotating shaft 108, the infusion needle 11 will be displaced laterally in the one or the other direction due to the cooperation of the worm screw 110 and the rack 112 of the turntable 20. Again, the rotating shafts 107, 108 are guided in a common sheath 103 along with the conduit 119 for the infusion liquid (or, in the case of a long, flexibly bendable infusion needle, along with the long needle—not shown).

In FIGS. 18 and 19, the action of the pull wires 105, 106 and the rotating shaft 108 make it possible to laterally displace the tip end of the infusion needle 11 between two different penetration areas and/or from a first penetration site to a second penetration site within a single penetration area.

Figure 20:
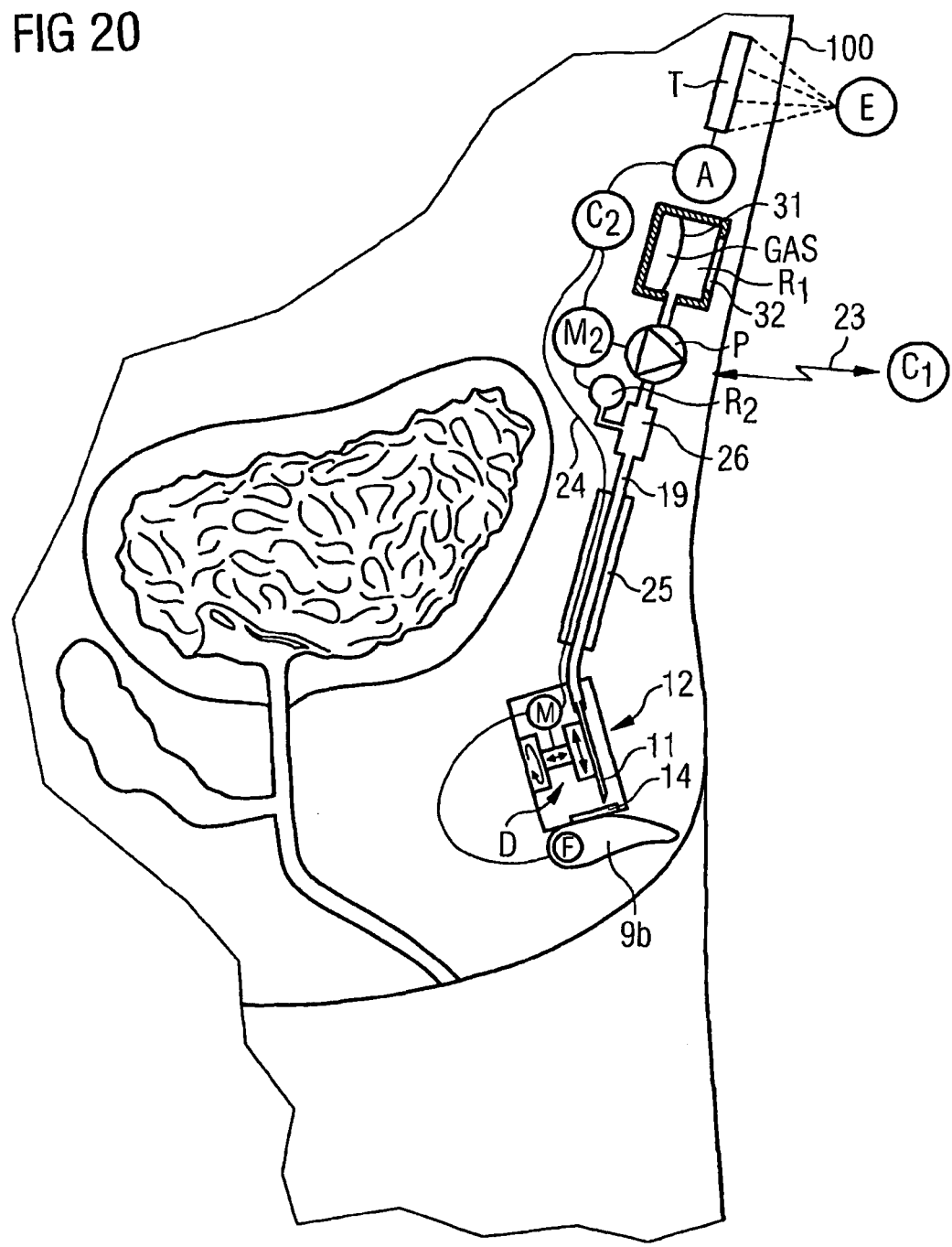
FIG. 20 shows the overall system of the invention implanted in a patient's body according to a first variation.

FIG. 20 shows a first variation of an overall system comprising any one of the first to twelfth embodiment described above. Specifically shown in the variation shown in FIG. 20 is a housing 12 with a single infusion needle 11 and a drive unit D as described in relation to FIG. 12. The housing 12 is implanted with its windows areas 14 positioned adjacent the corpora cavernosa 9a, 9b, of which window areas 14 only one is shown in FIG. 20. The dimensions in FIG. 20 are far from being true to scale and merely serve illustrative purposes. A motor M is contained in the housing 12 for driving the drive unit D. While the motor M in the housing 12 may be designed to move the tip end of the infusion needle 11 in all directions as indicated in FIG. 20, it is particularly preferable in context with a long, flexibly bendable infusion needle to cause advancement and retraction of the front end of the long infusion needle by advancing and retracting the entire infusion needle from its rear end using an additional motor, so as to minimize the motor size in the housing 12 for reasons of space constraints in the injection area. The additional motor may be accommodated in a separate second housing—not shown in FIG. 20—along with the rear end of the long infusion needle and possibly along with further components remotely implanted in the patient's body. The motor M within the housing 12 (and likewise the afore-mentioned additional motor) is controlled by means of a control unit $C_2$ constituting the implantable part of a control system which further comprises an external data processing device $C_1$ by which commands and any other kind of data can be sent to the control unit $C_2$. For instance, the external data processing device $C_1$ may be used to initiate an injection cycle from outside the patient's body, this being done wirelessly as indicated by arrow 23. The implanted control unit $C_2$ not only controls the motor M inside the housing 12 but also controls the energy supply from an accumulator A to the motor M inside the housing 12.

The external data processing device $C_1$ may likewise be used to program the implanted control unit $C_2$. Also, a data transfer port for transferring data between the external data processing device $C_1$ and the implanted control unit $C_2$ may be adapted to transfer data in both directions.

A feedback sensor F implanted inside the patient's clitoris is shown here as being connected to the motor M inside the housing 12 and may likewise be connected to the implantable control unit $C_2$. The feedback sensor F can sense one or more physical parameters of the patient, such as the drug level inside the corpora cavernosa, the flow volume through the corpora cavernosa, the pressure inside the corpora cavernosa and the like. Other feedback sensors may be provided at a different location so as to sense process parameters of the system, such as electrical parameters, distention, distance and the like.

The conduit 19 connecting the needle 11 with a reservoir comprising compartments $R_1$ and $R_2$ and the wiring 24 for transmitting electric energy from the energy source A to the motor M inside the housing 12 are guided through a common conduit 25. Alternatively, where a long and flexibly bendable needle is used, the conduit 19 may guide the long infusion needle 11 between the reservoir and the housing 12.

In the variation of the entire system shown in FIG. 20, the reservoir comprises a first compartment $R_1$ with e.g. a saline solution included therein, and a second compartment $R_2$ with e.g. a drug in powder form or freeze-dried form included therein. A pump P driven by a second motor $M_2$ is arranged to pump infusion liquid from the reservoir $R_1$ to the infusion needle 11. The infusion liquid pumped by the pump P will pass through a mixing chamber 26 into which drugs will be released from the reservoir $R_2$ in appropriate time coordination. The motor $M_2$ or a different motor may cause the drugs to be released from the second reservoir $R_2$. The motor $M_2$ is also controlled by the control unit $C_2$. Thus, infusion liquid pumped via the pump P from the relatively large first reservoir $R_1$ through the mixing chamber 26, in which it is mixed with the drugs released from the second reservoir $R_2$, will reach the infusion needle 11 which has meanwhile penetrated the self-sealing window area 14 of the housing 12 and will flow into the corpus cavernosum 9b.

In addition to or instead of the control unit $C_2$, a pressure sensitive switch for activating the motor M inside the housing 12 and/or the motor $M_2$ may be arranged subcutaneously.

Although the embodiment shown in FIG. 20 may comprise one of a great variety of reservoir types, a particular reservoir type will now be described. The volume of the reservoir $R_1$ is divided into two sections by means of a membrane 31. One section is filled with gas whereas the other section is filled with the infusion liquid (saline solution). An infusion port 32 allows for refilling the reservoir $R_1$ with infusion liquid by means of a replenishing needle. When the reservoir $R_1$ is in its full state, the gas section is at ambient pressure or over-pressurized. As infusion liquid is drawn from the reservoir $R_1$ by means of the pump P upon each infusion cycle, the pressure in the gas section will decrease below ambient pressure, i.e. to a negative relative value. Depending upon the particular type of pump P, it may be advantageous to provide a single acting ball valve to prevent any backflow from the pump P to the reservoir $R_1$.

There are various ways of providing the motors M and $M_2$ with energy. In the variation shown in FIG. 20, energy is supplied from outside the patient's body either for direct use by the motors and/or for charging the accumulator A, which may be in the form of a rechargeable battery and/or a capacitor. An extracorporal primary energy source E transmits energy of a first form through the patient's skin 100 to an energy transforming device T which transforms the energy of the first form into energy of a second form, such as electric energy. The electric energy is used to recharge the accumulator A which provides secondary energy to the motor M upon demand.

The external primary energy source E may be adapted to create an external field, such as an electromagnetic field, magnetic field or electrical field, or create a wave signal, such as an electromagnetic wave or sound wave signal. For instance, the energy transforming device T as shown in FIG. 20 may act as a solar cell, but adapted to the particular type of wave signal of the primary energy source E. The energy transforming device T may also be adapted to transform temperature changes into electrical energy.

Instead of the external primary energy source E, an implantable primary energy source E may be used, such as a regular long-life battery instead of the accumulator A.

The energy signal may also be used to transmit signals from the external data processing device $C_1$ by appropriate modulation of the energy signal, regardless of whether the energy is transmitted wirelessly or by wire, the energy signal thereby serving as a carrier wave signal for the digital or analog control signal. More particularly, the control signal may be a frequency, phase and/or amplitude modulated signal.

Figure 21:
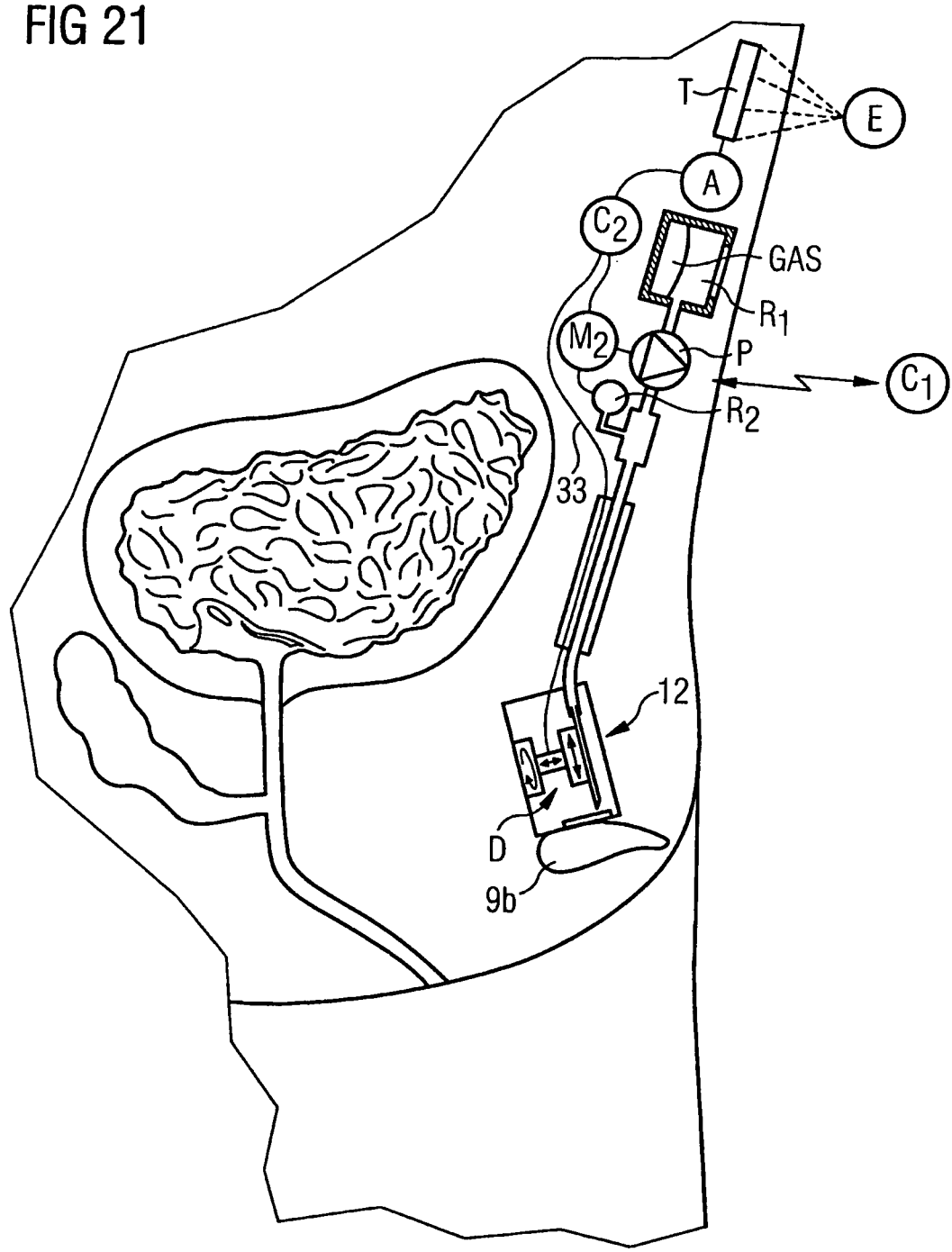
FIG. 21 shows the overall system of the invention implanted in the patient's body according to a second variation.

FIG. 21 shows a second variation of the entire system which basically differs from the system of FIG. 20 only in that the motor M inside the housing 12 is dispensed with. Instead, the motor $M_2$ is used to drive the drive unit D. This is achieved by means of a rotating shaft 33 in the form of an elastically bendable worm screw, the rotating shaft 30 replacing the wiring 24 of the system shown in FIG. 20. Alternatively, where the infusion needle 11 is long and flexible, the infusion needle may be advanced by engagement of two helical gears, one of which being formed on the rear end of the infusion needle, or by a similar gearing cooperating with the infusion needle's rear end.

Figure 22:
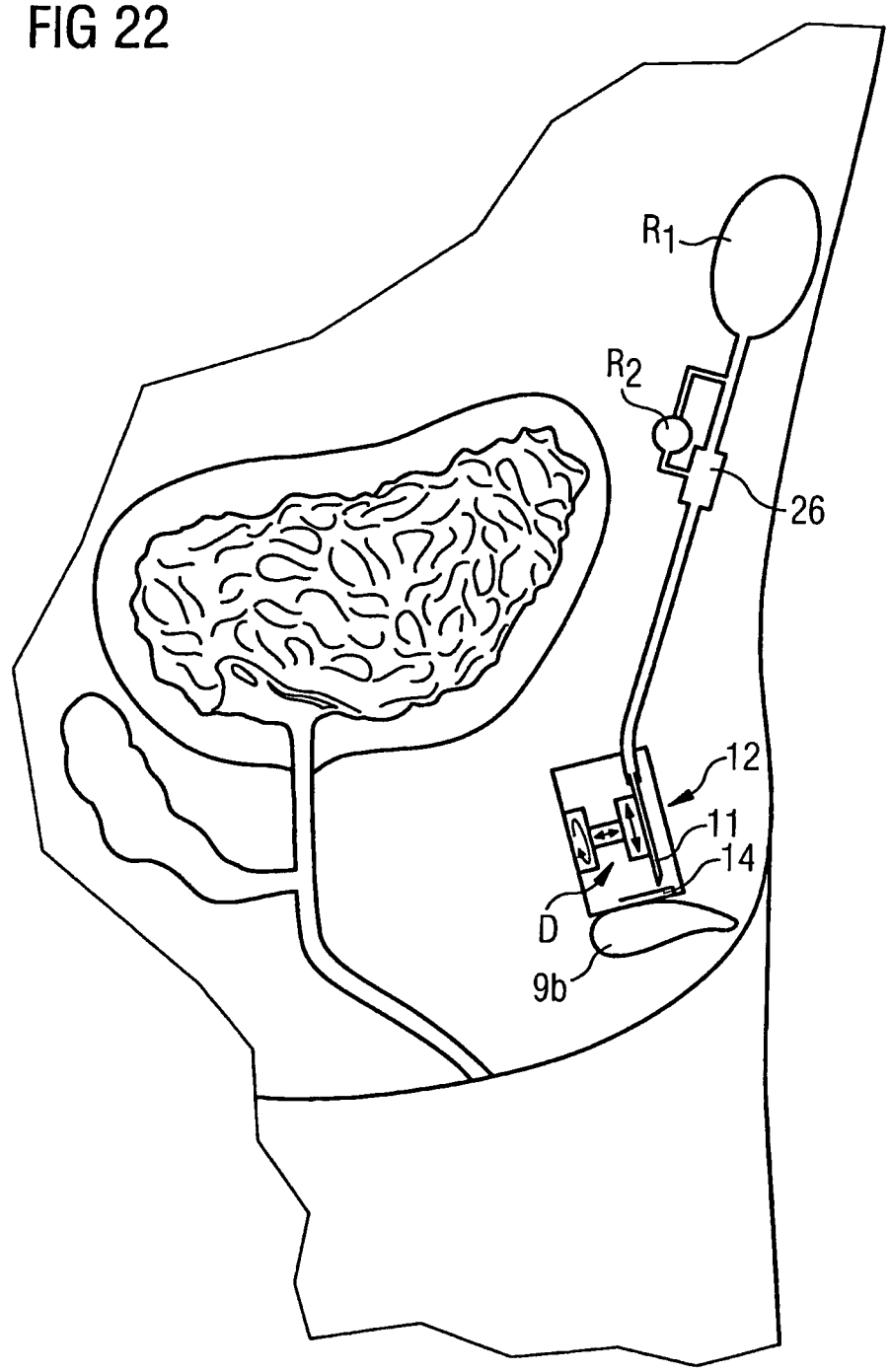
FIG. 22 shows the overall system of the invention implanted in the patient's body according to a third variation.

FIG. 22 shows a third variation of the entire system which operates purely mechanically. The reservoir $R_1$ containing the infusion liquid, i.e. the saline solution, is of balloon type, thereby functioning both as a reservoir and as a pump if it is compressed manually from outside the patient's body. The pressure generated in the reservoir $R_1$ will act on the reservoir $R_2$ containing the drug. Upon a certain pressure, the drug will be released from the reservoir $R_2$ into the mixing chamber 26 and upon further increase of the pressure the infusion liquid will be allowed to enter the mixing chamber 26, mix with the drug released from the reservoir $R_2$, flow towards the infusion needle 11, and build up pressure on the infusion needle 11 such that the drive unit D is caused to advance the infusion needle 11 through the self-sealing window area 14 into the patient's corpus cavernosum. Once the pressure is released, the infusion needle 11 will retract automatically due to mechanical spring forces or the like and move into a different position in which it can penetrate the second of the two self-sealing window areas 14 when the reservoir $R_1$ is compressed again. Where two infusion needles 11 are provided, a single compressing action on the reservoir $R_1$ would be sufficient to inject the drug into both the left and right corpora cavernosa.

Figure 23:
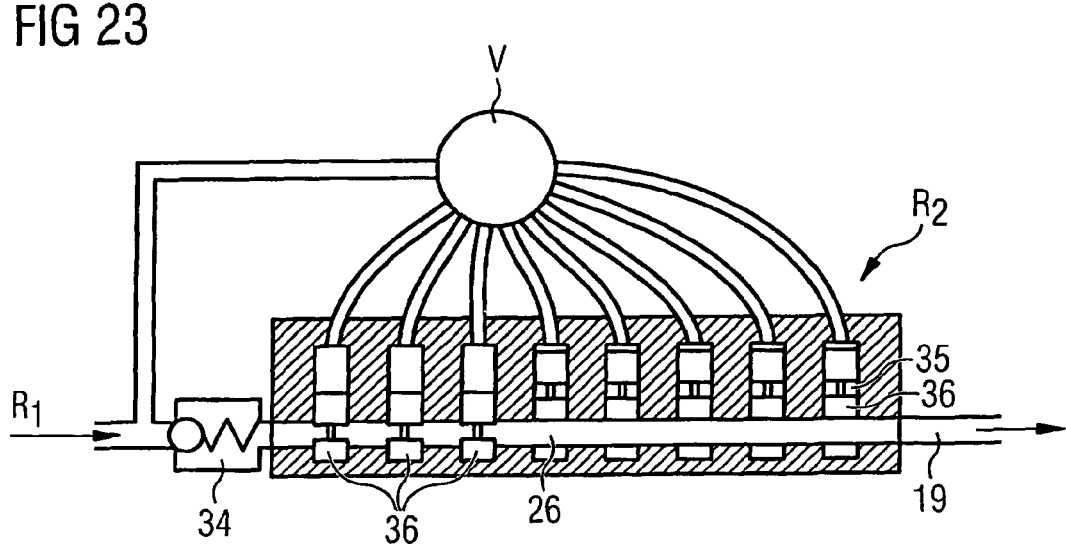
FIG. 23 shows drug compartments as part of the reservoir of the system according to a first principle.

FIG. 23 shows a first principle of how drugs within a plurality of compartments 34 of the reservoir $R_2$ can be released one at a time by a purely hydromechanical solution. As the infusion liquid is urged from the reservoir $R_1$ towards the conduit 19 leading to the infusion needle or needles, it is first blocked by a spring-loaded ball valve 34 which opens only when a certain pressure is exceeded. The pressure building up in front of the ball valve 34 is guided by means of a stepper valve V sequentially onto one of a plurality of compartments 35. The compartments are each formed as a cavity 35 within a piston 36. Once a certain pressure is exceeded, the piston 36 will be pushed into a position where the compartment 35 is in flow communication with a mixing chamber 26. In the state shown in FIG. 23, three pistons 36 have already been pushed into such position. When the pressure in the reservoir $R_1$ is further increased, the spring force of the ball valve 34 will be overcome and the infusion liquid urged from the reservoir $R_1$ towards the conduit 19 will take with it the drug that has been released into the mixing chamber 26.

Figure 24:
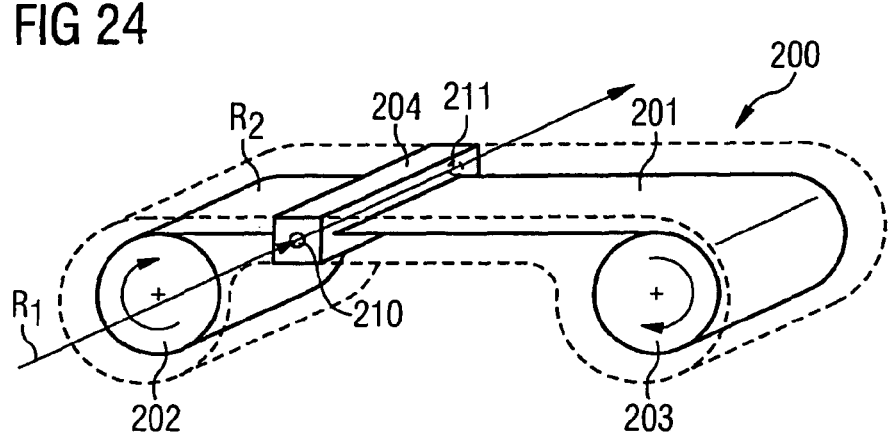
FIG. 24 shows drug compartments mounted on a tape wound on a reel in a replaceable cassette as part of the reservoir of the system according to a second principle.
Figure 25:
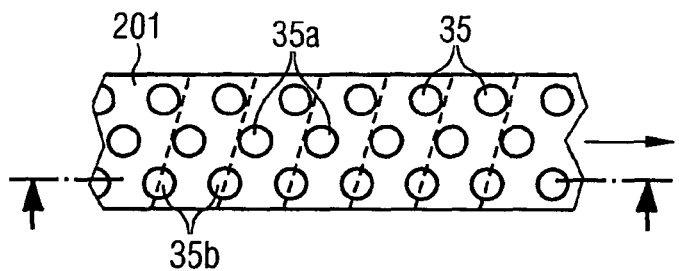
FIG. 25 shows a part of the tape of FIG. 20 in greater detail.
Figure 26:
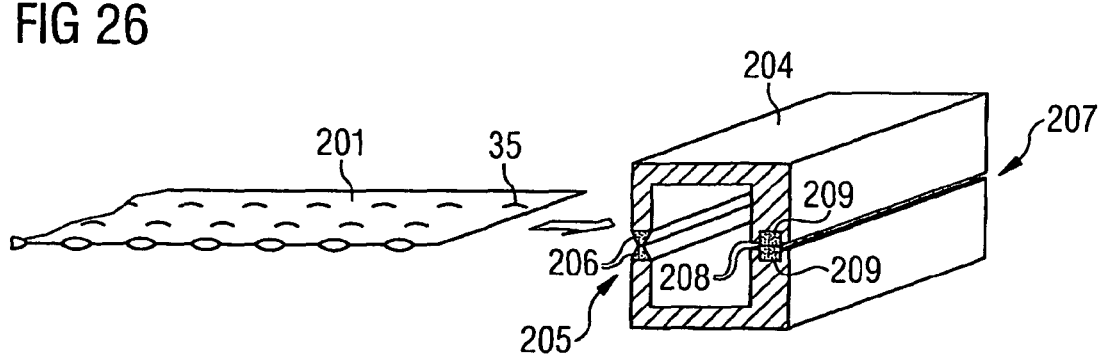
FIG. 26 shows the principle of operation of the replaceable cassette of FIG. 24.

FIGS. 24 to 26 show a second principle of realizing the reservoir $R_2$ comprising a plurality of small drug compartments 35, 35a, 35b. The drug compartments are integrally formed in a tape 201 which is wound on a first reel 202 and can be unwound from said first reel 202 onto a second reel 203. The reels 202, 203 and the tape 201 are contained in a cassette 200 which may be inserted in the entire system so as to form part of the reservoir. The cassette 200 is preferably replaceable.

As can be seen in FIG. 25, the compartments 35, 35a, 35b containing the drug e.g. in powder form or freeze-dried form are arranged in a plurality of rows as seen in the transporting direction (indicated by the arrow). However, the compartments 35 of one row are a certain distance offset in the transporting direction from the compartments 35a and 35b of the other rows. Thus, when the tape 201 is wound from reel 202 to reel 203, it is guided through a conduit 204 forming part of the cassette 200 through which the infusion liquid is pumped from the reservoir $R_1$ to the infusion needle or needles, and the compartments 35, 35a, 35b will enter the conduit 204 one after the other.

While it is conceivable to open one of the compartments 35, 35a, 35b that has entered the conduit 204 by mechanical action, such as a hammer or piercing element, the opening of the compartments 35 in the embodiment shown in FIGS. 24 to 26 needs no further action other than winding the tape 201 onto the reel 203. That is, as can be seen from FIG. 26, when the tape 201 enters the conduit 204 through a first slit 205, the compartments 35 will not be damaged due to the fact that the slit 205 is relatively wide and is closed by two soft sealing lips 206. However, when the tape 201 exits the conduit 204 on the other side thereof, it will have to pass a narrower second slit 207 with front edges 208 that are not resilient. The compartments 35 will therefore burst on their way out of the conduit 204 when they slip between the edges 208 of the narrow slit 207. Soft seals 209 in the slit 207 prevent liquid from leaking from the conduit 204.

The entry 210 and the exit 211 of the conduit 204 within the cassette 200 each include a valve that automatically closes when the cassette 200 is removed from the system and automatically opens when the cassette 200 is installed in the system. This allows for replacement of the cassette 200 without adversely affecting the remaining components of the overall system.

Figure 27:
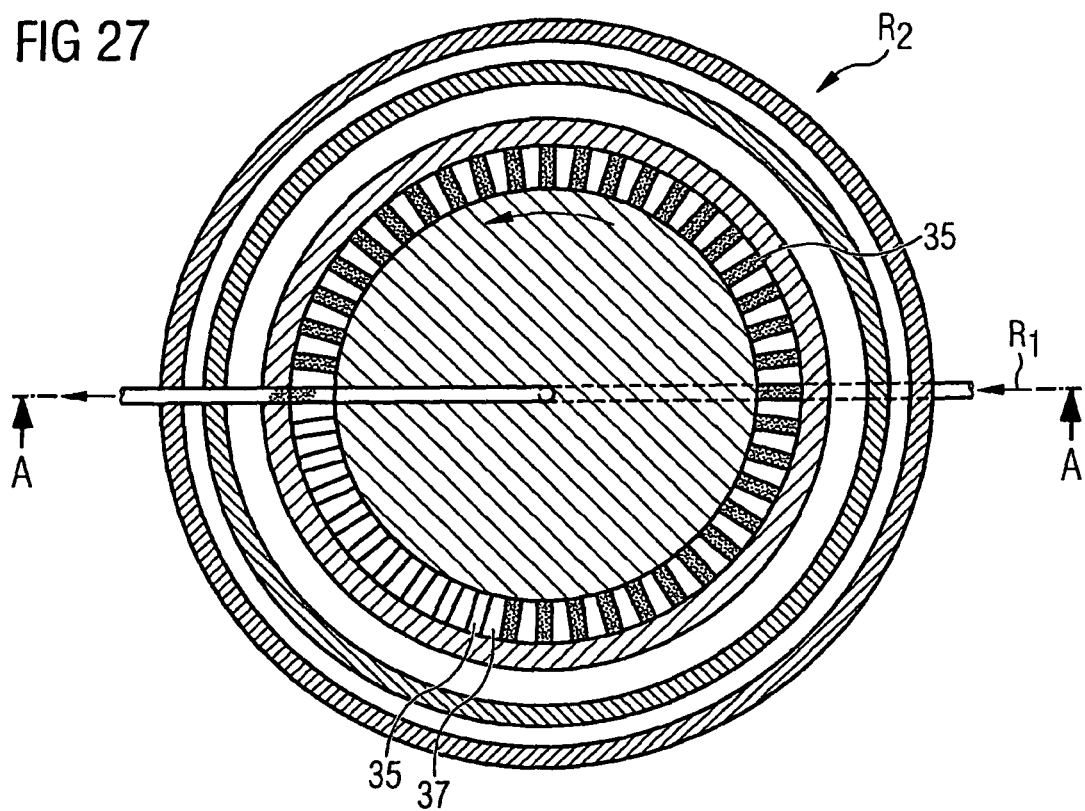
FIG. 27 shows drug compartments as part of the reservoir of the system according to a third principle.
Figure 28:
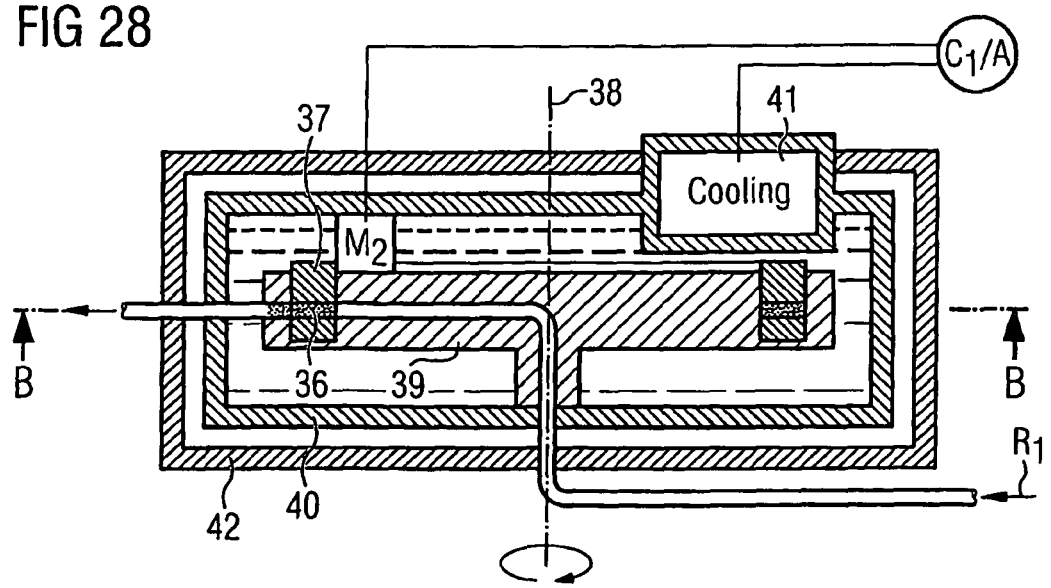
FIG. 28 shows a cross-sectional view of the drug compartments of FIG. 27 including an insulation chamber and cooling device.

FIGS. 27 and 28 show a third principle of realizing the reservoir $R_2$ comprising a plurality of small drug compartments 35. While FIG. 27 shows a cross-sectional plan view according to section BB in FIG. 28, FIG. 28 shows a cross-sectional side view thereof according to section AA in FIG. 27. The compartments 35 containing the drug in powder form or freeze-dried form are arranged in a rotatable plate 37. A motor $M_2$ is provided to rotate the plate 37 about an axis 38. The motor $M_2$ is controlled to advance the plate 37 stepwise so as to bring one compartment 35 at a time in line with the conduit 39 connecting the reservoir $R_1$ containing the saline solution with the infusion needle or needles. Energy is supplied to the motor $M_2$ from the accumulator A via the control unit $C_1$.

The rotatable plate 37 is mounted in a fixed base plate 39 which itself is fixedly mounted in a housing 40 insulating the base plate 39 and the rotatable plate 37 thermally against an outer housing 42. A cooling device 41 is provided to cool a liquid surrounding the base plate 39 and rotatable plate 37 down to a temperature below 37° C. This serves to protect the drugs inside the compartment 36 from degrading too quickly. The accumulator A supplies the cooling device 41 with energy.

Figure 29:
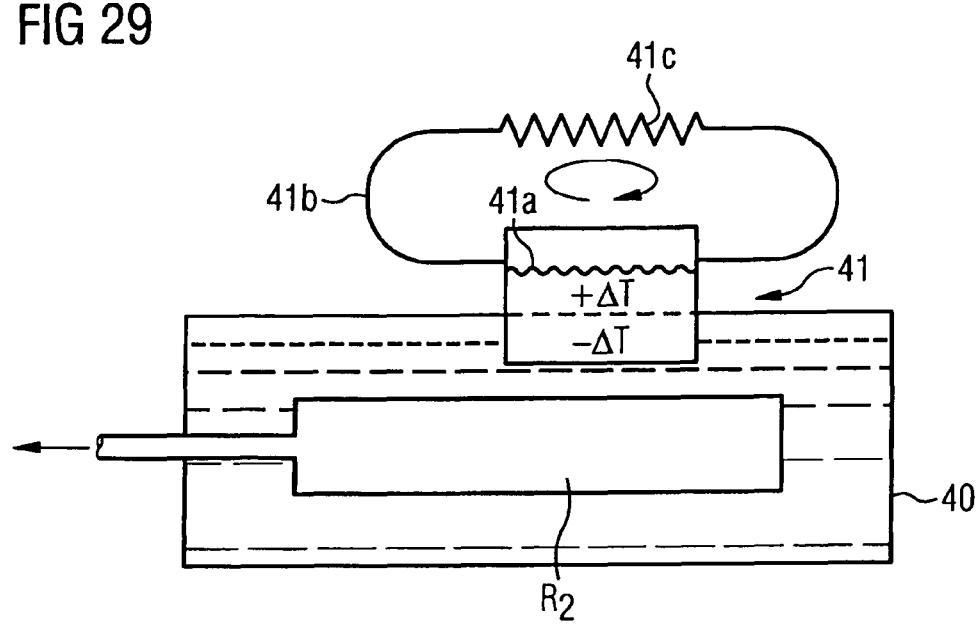
FIG. 29 shows the principle of the cooling device of FIG. 28 in combination with a heat exchanger.

FIG. 29 shows a general principle of cooling the reservoir $R_2$ containing the drug to be cooled. The cooling device 41 may be an electrothermal cooler, i.e. based on the Peltier effect consuming electric energy, or may be of the refrigerator type. Accordingly, the cold part of the cooler 41 is placed on the side to be cooled whereas the warm part of the cooling device 41 is placed on the other side so that the heat energy can be dissipated to the outside. An increased surface 41a on the warm side of the cooling device 41 serves to increase heat dissipation. Furthermore, a heat exchanging fluid may be passed through a conduit 41b along the increased surface 41a to transfer the dissipated heat energy to a remote location within the patient's body where the heat is dissipated into the patient's body through a specific heat exchanging surface 41c.

Figure 30:
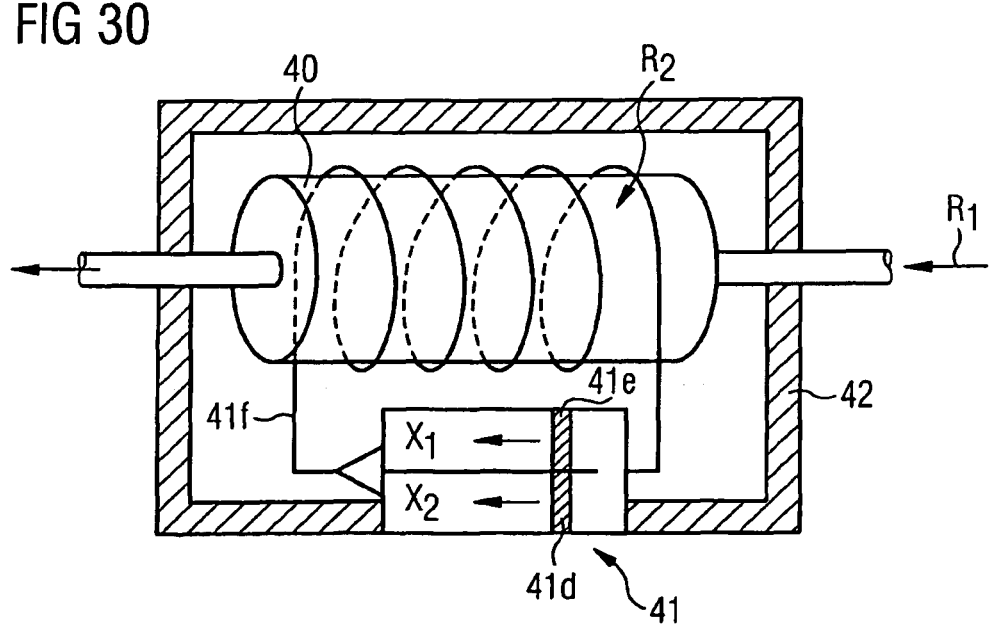
FIG. 30 shows a specific embodiment for the cooling device of FIG. 28.

FIG. 30 shows a different principle of cooling the drugs contained in the reservoir $R_2$. In this embodiment, two chemicals X1 and X2 are contained separate from each other in respective compartments of the cooling device 41. When the chemicals X1 and X2 are brought together, they will react with each other and such reaction will consume energy which is absorbed as thermal energy from the surroundings. By means of two pistons 41d, 41e, the chemicals X1, X2 are dispensed into a cooling line 41f in a controlled manner, which cooling line is preferably in contact with the housing 40 containing the reservoir $R_2$. The chemical mixture X1-X2 displaced within the cooling line 41f will flow back into the chamber containing the chemicals X1, X2, but onto the other side of the pistons 41d, 41e.

Figure 31:
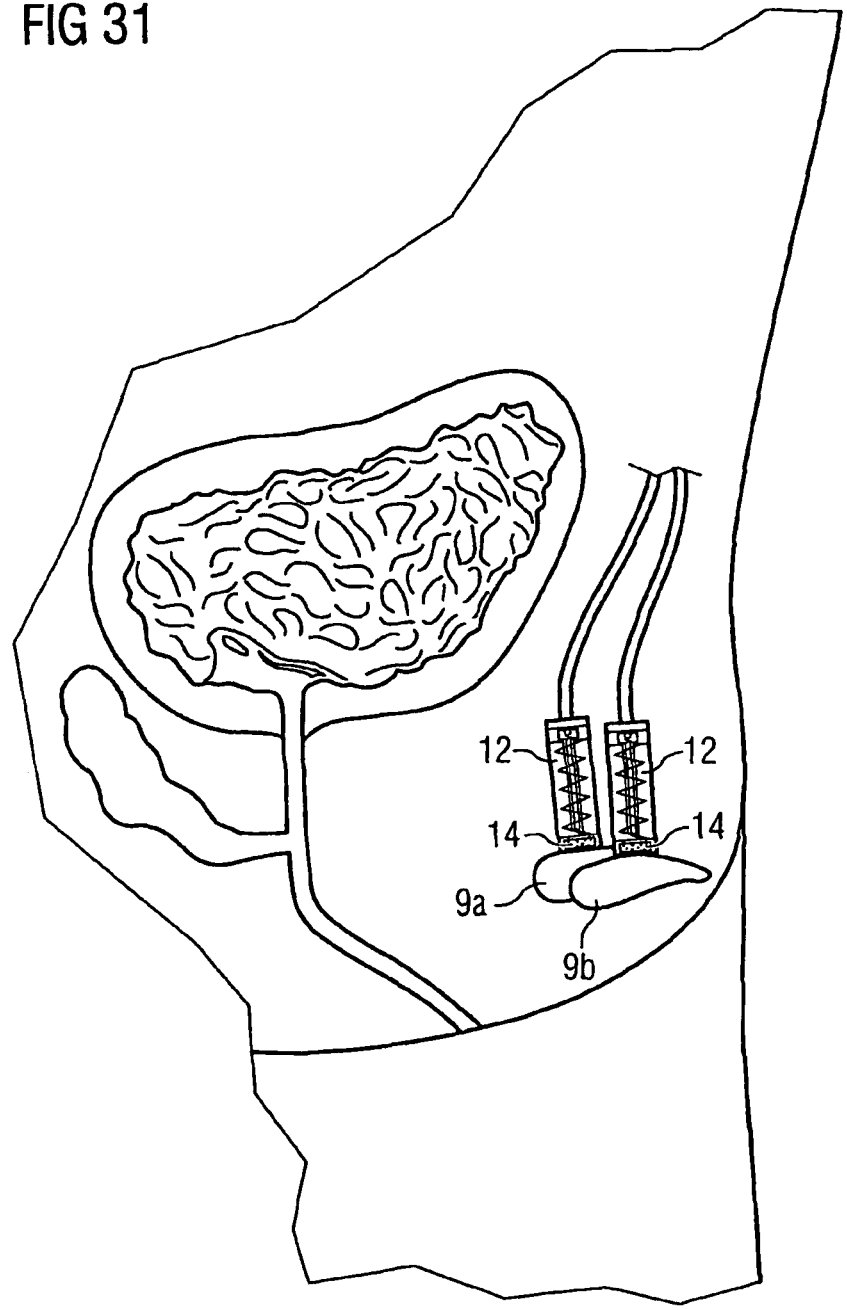
FIG. 31 shows a part of the system implanted in the patient's body comprising separate needles for the right and the left corpus cavernosum, FIG. 32 diagrammatically shows the system of FIG. 31, FIG. 33 diagrammatically shows the system of FIG. 30 with a long, flexibly bendable infusion needle.
Figure 32:
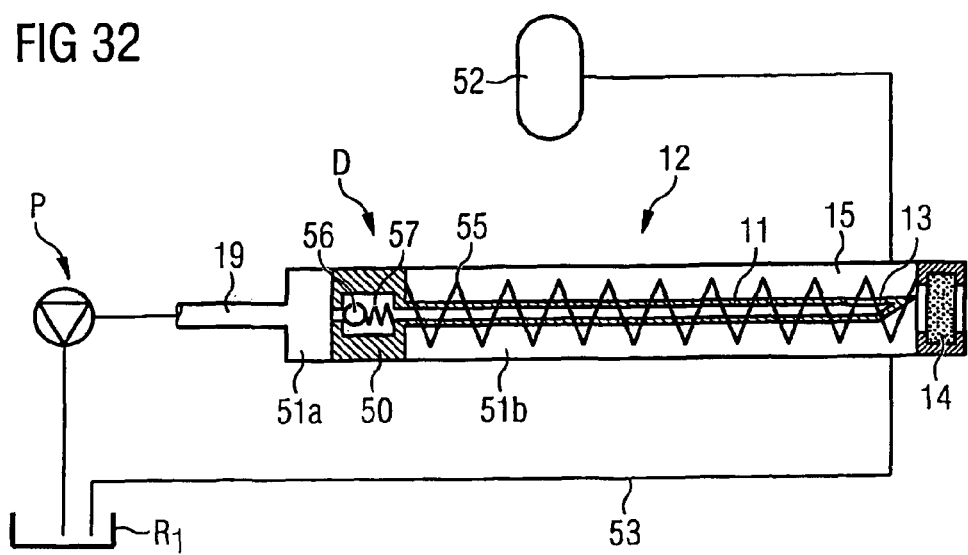

A further embodiment is shown in FIG. 31. In this embodiment, again, two separate needles are provided, one infusion needle for each of the left and right corpora cavernosa. However, unlike the previously discussed embodiments, the two needles each have their own housing 12 implanted in the patient's body with their respective self-sealing window area 14 adjacent the left and right corpora cavernosa, respectively. This principle is shown in FIG. 32 in more detail with respect to one of the two needles. The drive unit D comprises a piston 50, to which the hollow infusion needle 11 is attached. The piston 50 separates a first chamber 51a in front of the piston 50 and a second chamber 51b behind the piston 50. While the pressure in the first chamber 51a corresponds to the pressure exerted by the pump P, the pressure in the second chamber 51b can be kept at a lower value. The second chamber 51b may be filled with a liquid, such as the infusion liquid, and the liquid may be urged into a flexible volume 52. The flexible volume 52 could be of simple balloon type so as to fill up without exerting any strong counterforce.

Instead of the flexible volume 52, a conduit 53 may connect the second chamber 51b with the reservoir $R_1$. Thus, when the needle 11 is advanced, liquid will be dispelled from the second chamber 51b through the conduit 53 into the reservoir $R_1$, and as the needle 11 is retracted by means of a return spring 55, liquid will be drawn from the reservoir $R_1$ through the conduit 53 back into the second chamber 51b.

The injection process is carried out as follows. As the pressure is increased in the first chamber 51a by means of the pump P, the needle 11 will be displaced against the force of the spring 55 of the drive unit B. Thus, the tip end 13 of the infusion needle 11 will penetrate through the self-sealing window area 14 press-fitted into the wall 15 of the housing 12 and will further penetrate any fibrosis having built up in front of the housing. When the return spring 55 is completely compressed and the pressure built up by the pump P is further increased, a ball valve 56 will be displaced against a second return spring 57 which is stronger than the first return spring 55. That way, as long as the pressure is held at a sufficiently high level, infusion liquid will be pumped from the reservoir $R_1$ through the conduit 19, the hollow infusion needle 11 and the needle's laterally arranged exit port into the patient's body. Upon pressure release, the ball valve 56 will close due to the return springs 55 and 57, and then the needle 11 will be retracted to its initial position shown in FIG. 23.

Figure 33:
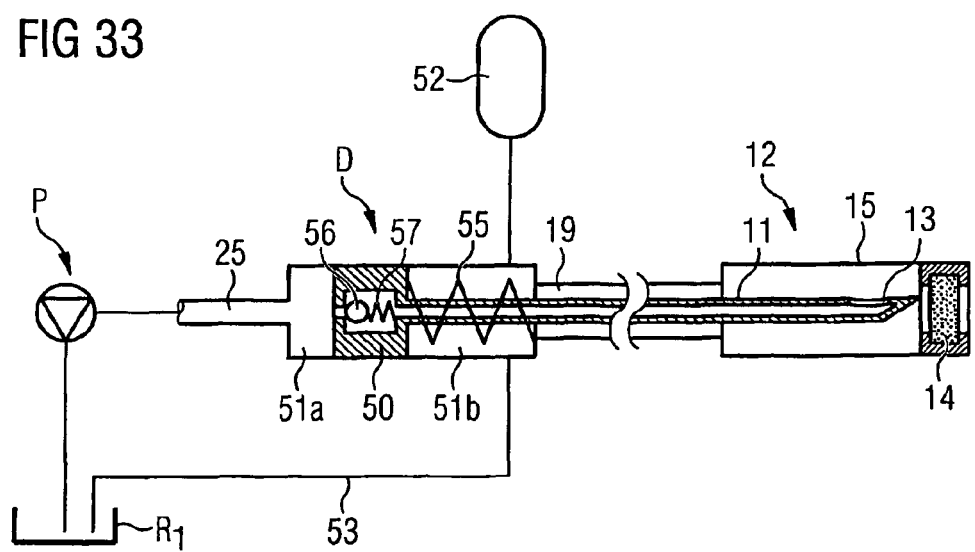

FIG. 33 shows the same principle, however, employing long, flexibly bendable infusion needle with only their respective front ends accommodated in the housing 12. As the pressure is increased in the first chamber 51*a* by means of the pump P remote from the housing 12 accommodating the tip end 13 of the infusion needle 11, the entire infusion needle 11 which is guided in the conduit 19 will be displaced against the force of the spring 55 of the drive unit B.

Figure 34:
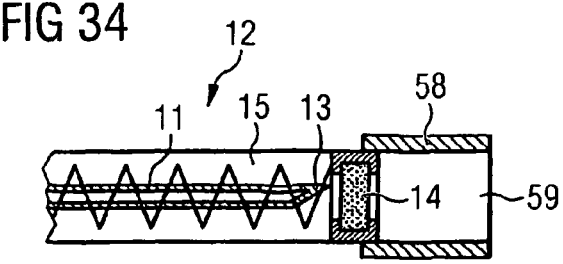
FIG. 34 shows a part of the system of FIGS. 32 and 33, respectively, including a tube into which the needle can be advanced.

It may be advantageous not to pierce any living tissue by means of the injection needle 11 once it is advanced through the outer wall 15 of the housing 12. Therefore, as shown in FIG. 34, a tube 58 may be placed in front of the window area 14. The cross-sectional form of the tube 58 may be adapted to the cross-sectional form of the window area 14, i.e. where the window area 14 is rectangular, the tube 58 likewise has a rectangular cross-section.

The exit end of the tube 58 has an open area 59 sufficiently large to prevent growth of fibrosis from spanning over the open area. Fibrosis will slowly grow into the tube along the tube's inner surface, before it reaches the window area 14 after a relatively long time. The tip end 13 of the needle 11 will therefore not have to penetrate any fibrosis during the first while after implantation of the system. Preferably, the open area 59 has an opening width of at least 3 mm. The length of the tube 58 may be in the range of 4 mm to 30 mm. The opening width 59 and the length of the tube 58 should be adjusted such that the substance injected into the tube 58 can safely seep into the patient's body. Thus, the longer the tube is, the larger the opening width thereof should be.

Figure 35A:
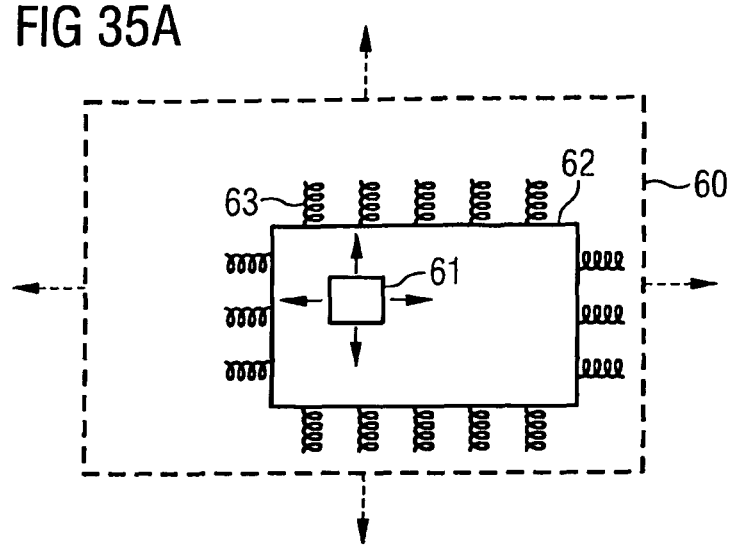
FIGS. 35A to 35C show a first and second embodiment for electromagnetically displacing the infusion needle in a plurality of lateral directions.
Figure 35B:
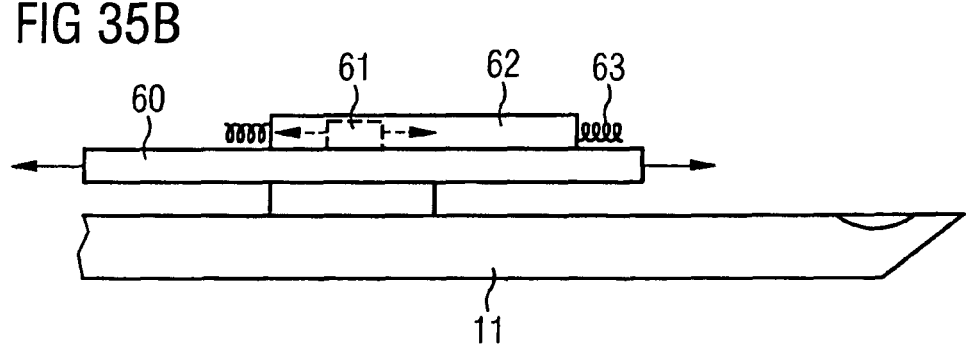

FIGS. 35A and 35B show a first embodiment for displacing the tip end of the infusion needle 11 in two or more different directions, i.e. a two-dimensional displacement. More specifically, FIG. 35A shows a plan view, whereas FIG. 35B shows a side elevational view schematically. As can be seen, a plate 60 to which the infusion needle 11 is fixedly mounted has a projection 61 extending into a frame 62 within which the projection 61 is free to move in any direction. Electromagnetic coils 63 are mounted on the sides of the frame 62 and are individually energizable. The electromagnetic coils 63 constitute the first part of an electromagnetic drive whereas the projection 61 is configured to constitute the second part of the electromagnetic drive. Thus, when one or more of the electromagnetic coils are energized, an electromagnetic field is created in the frame 62 and the electromagnet second part, i.e. the projection 61, will adjust its position within such field accordingly. Due to the fact that the infusion needle 11 is fixedly mounted to the plate 60, the infusion needle 11 will move along with the projection 61. This way, the infusion needle 11 can be advanced and retracted and can also be displaced laterally.

Of course, the infusion needle 11 may be attached to the electromagnetic drive in a different manner, e.g. perpendicular to the plane defined by the electromagnetic coils 63 (rather than in parallel as in FIG. 35B). As a result, the infusion needle would be laterally displaceable in a plurality of directions (rather than being advanceable and retractable).

Figure 35C:
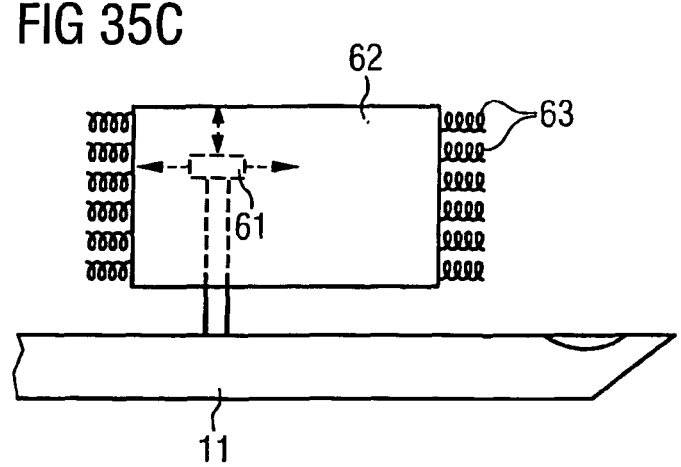

Alternatively, the electromagnetic drive may be such as to displace the infusion needle in any lateral direction and, in addition, to advance and retract the infusion needle. This can be achieved e.g. with a structure as schematically shown in FIG. 35C relating to a second embodiment for displacing the tip end of the infusion needle 11. FIG. 35C shows an elevational side view similar to FIG. 35B, but the electromagnetic coils 63 do not define a single plane, but rather a plurality of planes is defined one above the other by providing additional electromagnetic coils 63 in a vertical direction. The top plan view would be similar to FIG. 35A. This way, the electromagnet second part 61 fixedly connected to the needle 11 moves within a three-dimensional frame 62 depending on the energization of respective ones of the magnetic coils 63.

Figure 36A:
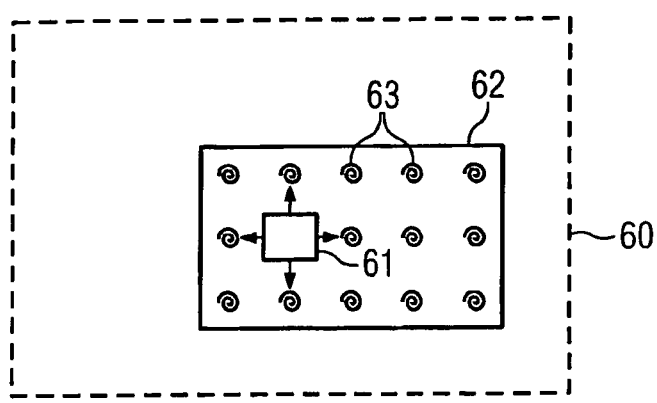
FIGS. 36A and 36B show a third embodiment for electromagnetically displacing the infusion needle in a plurality of lateral directions.
Figure 36B:
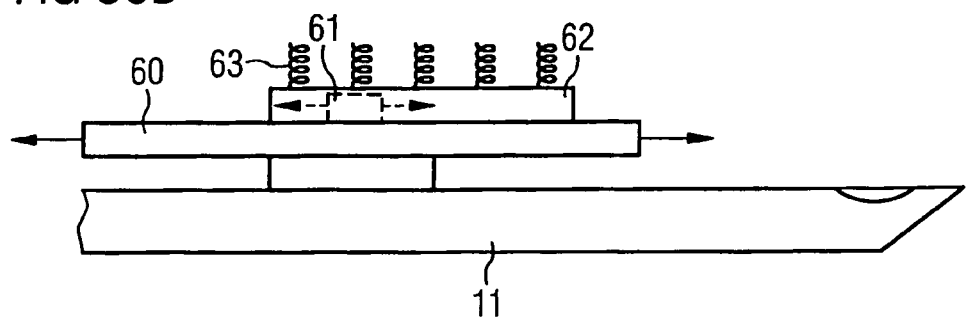

FIGS. 36A and 36B show a plan view and a side view of a third embodiment of an electromagnetic drive for moving the infusion needle 11 in a plurality of directions. In this embodiment, the electromagnetic coils 63 constituting the electromagnet first parts are arranged in a first plane and the electromagnet second part constituted by the protrusion 61 fixedly connected to the infusion needle 11 via the plate 60 is movable in a plane in front of or behind the plane defined by the electromagnet first parts. However, the electromagnetic coils 63 are oriented differently in this third embodiment. Again, depending upon the energization of the individual electromagnetic coils, the electromagnet second part, i.e. the protrusion 61, will adjust its position in the created electromagnetic field within the frame 62.

Figure 37:
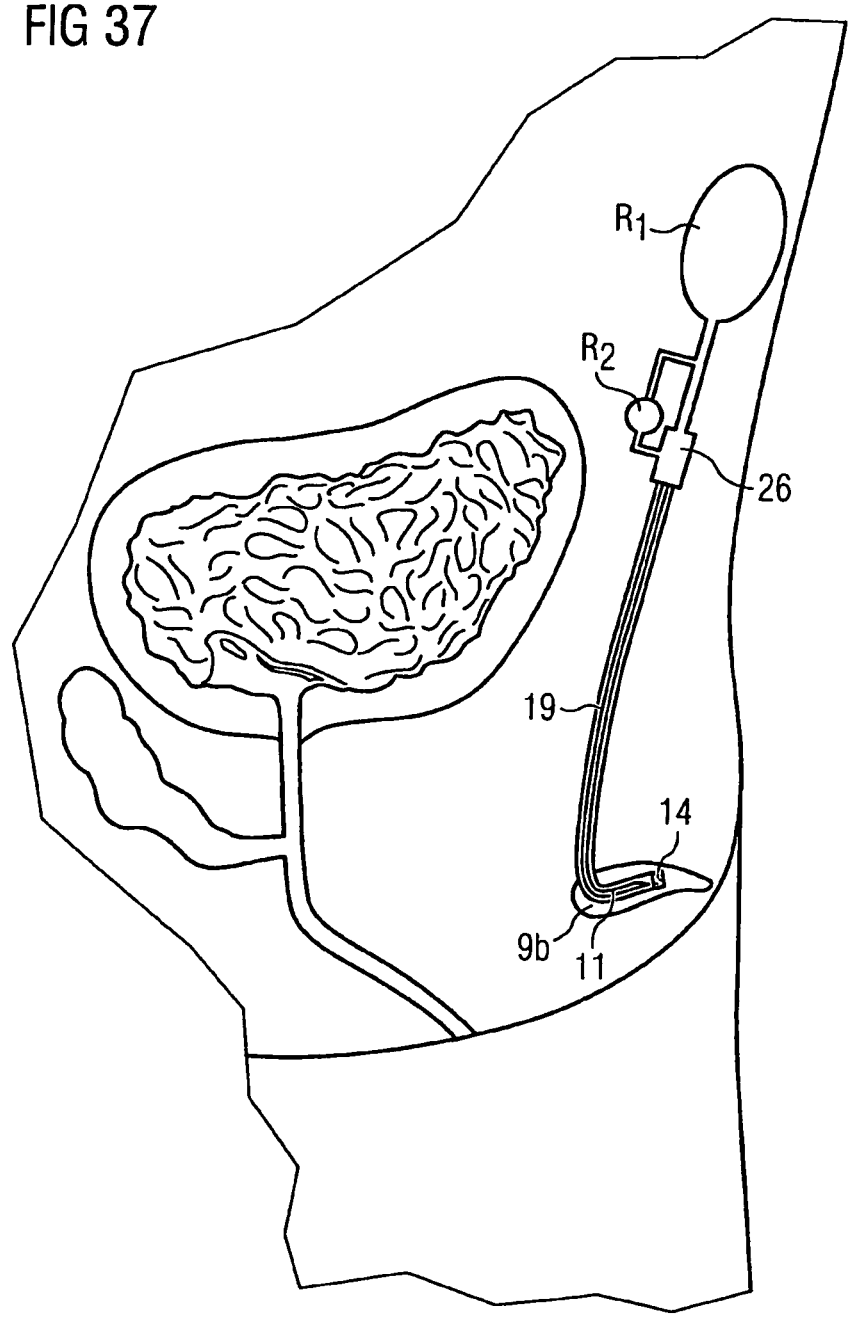
FIG. 37 shows the overall system of the invention implanted in a patient's body according to a fourth variation.

FIG. 37 shows an overall system of the invention implanted in a patient's body according to a fourth variation. This variation differs from the first to third variations described in relation to FIGS. 21 to 23 in that the infusion needle is not accommodated in a housing so as to be laterally displaceable. The infusion needle 11 is instead guided in a catheter 19 ending inside the patient's corpus cavernosum. Accordingly, two separate needles 11 are provided, which are long and flexibly bendable. They are advanced from the rear ends thereof so as to penetrate a window area 14 at the front end of the catheter, whenever a drug is injected to achieve an erection. While the variation shown in FIG. 37 is purely mechanic, similar to the variation shown in FIG. 23, the overall system may be more complex, e.g. similar to the variations described in relation to FIGS. 21 and 22.

Figure 38:
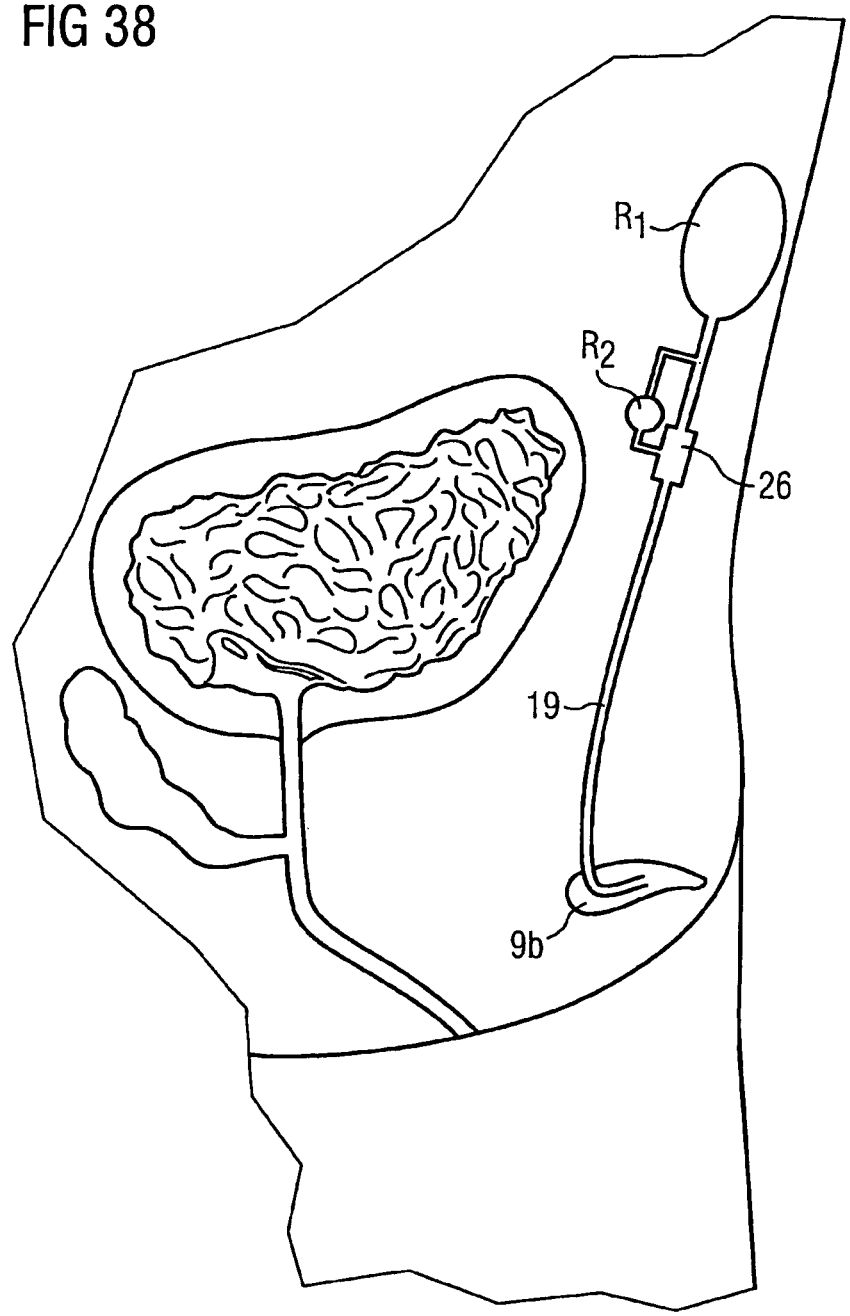
FIG. 38 shows the overall system of the invention implanted in the patient's body according to a fifth variation.

FIG. 38 shows an overall system of the invention according to a fifth variation which is similar to the afore-mentioned fourth variation, except that there is no needle provided in the catheter 19. The substances from the reservoirs $R_1$ and $R_2$ are delivered to the corpus cavernosum through the catheter 19. Accordingly, the catheter 19 has an open end or, more preferably, an end that can be opened when needed, e.g. mechanically as described above.

Figure 39:
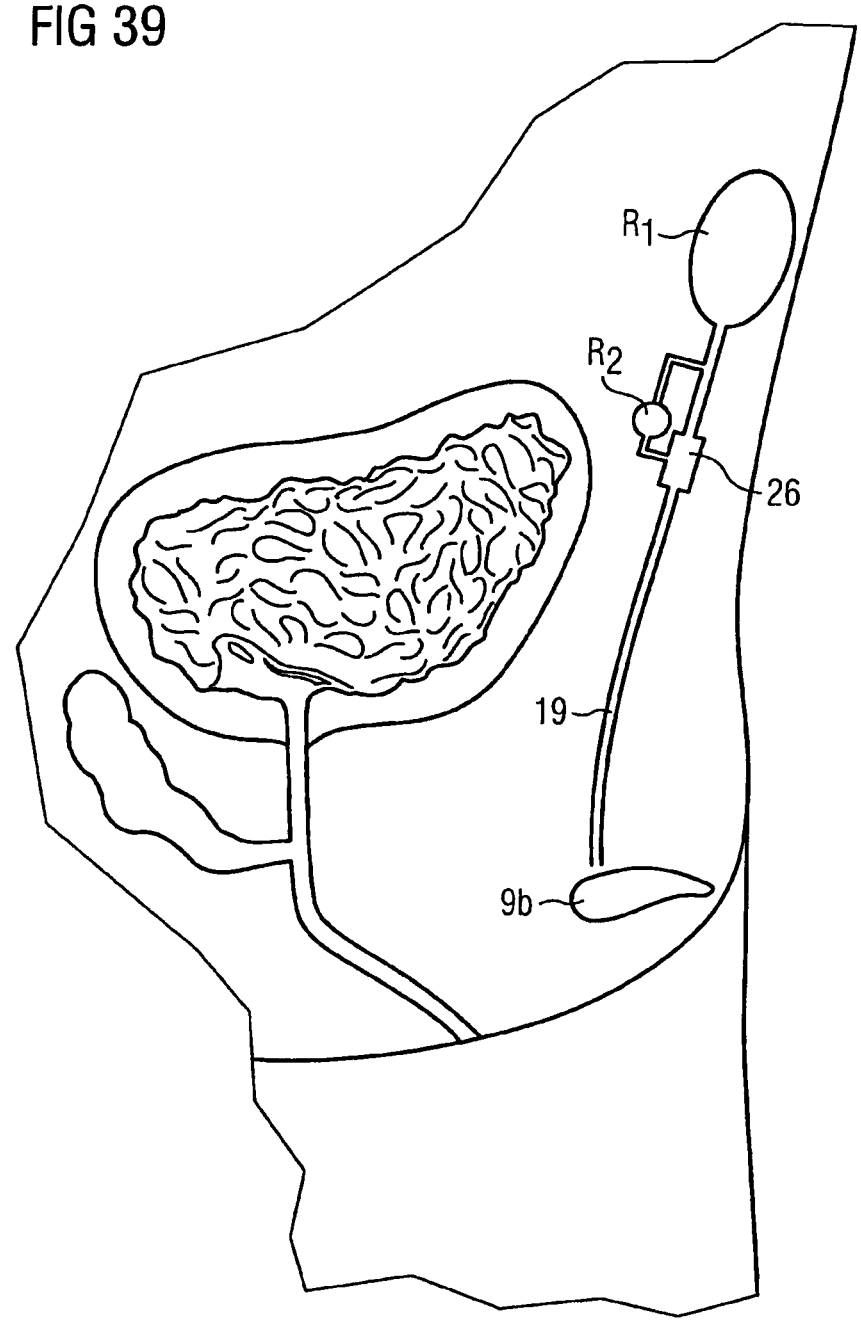
FIG. 39 shows the overall system of the invention implanted in the patient's body according to a sixth variation.

FIG. 39 shows an overall system of the invention according to a sixth variation which is similar to the afore-mentioned fifth variation, except that the catheter does not end in the corpus cavernosum, but ends in close proximity thereto, such as in muscle tissue regulating blood flow through the patient's left and right corpus cavernosum and/or in another kind of tissue in close proximity to the patient's left and right corpus cavernosum. Alternatively, the catheter 19 may guide an infusion needle, such as the infusion needle 11 as described in the fourth variation in relation to FIG. 37. Thus, when the catheter 19 is implanted, the drugs are delivered through the catheter 19 or through the infusion needle 11, as the case may be, outside the corpora cavernosa.

Figure 40:
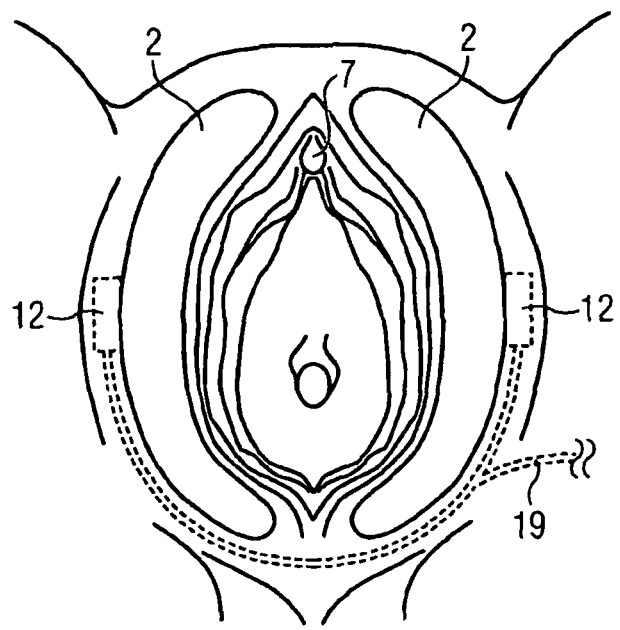
FIG. 40 shows the application of the system with injection needles on the bulbospongiosus muscles.

FIG. 40 shows the application of the system on the bulbospongiosus muscles 2. In this embodiment, two housings 12 are positioned adjacent the bulbospongiosus muscles 2, respectively. The housings 12 each accommodate one needle which, when advanced from the housing, penetrates into the muscle tissue.

Figure 41:
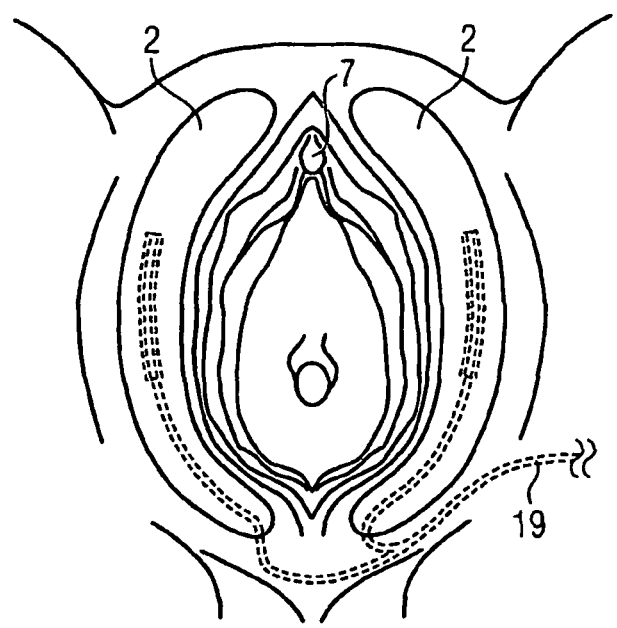
FIG. 41 shows the application of the system with catheters implanted in the bulbospongiosus muscle.

FIG. 41 shows the application of the system with two catheters implanted so as to terminate in the bulbospongiosus muscle 2. Drugs can drain from the catheter ends directly into the muscle tissue.

It should be appreciated that the features of all the above described variations and embodiments may be combined and/or inter-exchanged deliberately, unless this is technically impossible.

A method of treating a human being (or an animal) by implanting at least part of the system in the patient's body comprises the steps of cutting the skin, dissecting free an area near the left and right corpus cavernosum, placing the fully implantable drug delivery device within said dissected area with the a least one catheter arranged next to the left and right corpus cavernosum and/or the two deep arteries of the right and left corpus cavernosum and/or the bulbs of the vestibule and/or muscle tissue regulating blood flow through the patient's left and right corpus cavernosum and/or regulating blood flow through the bulbs of the vestibule, such as the ischiocavernosus and bulbospongiosus muscles, and/or another kind of tissue in close proximity to the clitoris, labia minora and/or bulbs of the vestibule, so as to allow for stimulation of erectile tissue by delivering a drug through said at least one catheter, and closing at least the skin after implantation of at least parts of the system.

A method of treating a human being (or an animal) may likewise comprise the steps of cutting the skin, dissecting free the left and right corpus cavernosum, placing the drug delivery device within said dissected area with the a least one catheter ending in the left and right corpus cavernosum and/or in the two deep arteries of the right and left corpus cavernosum and/or in the bulbs of the vestibule, so as to allow for stimulation of erectile tissue by delivering a drug through said at least one catheter, and closing at least the skin after implantation of at least parts of the system.

The method of treating a human being (or an animal) may particularly comprise the steps of cutting the skin, dissecting free a first area near the left and right corpus cavernosum, placing the at least one housing accommodating the at least one infusion needle within said dissected area such that the tip end of the at least one infusion needle can penetrate, when penetrating the housing's outer wall, into at least one of the left and right corpus cavernosum and/or into at least one of the two deep arteries of the right and left corpus cavernosum and/or into the bulbs of the vestibule and/or into muscle tissue regulating blood flow to the patient's left and right corpus cavernosum and/or regulating blood flow through the bulbs of the vestibule, and/or into another kind of tissue in close proximity to the clitoris, labia minora and/or bulbs of the vestibule allowing stimulation of erectile tissue, and finally closing at least the skin after implantation of at least parts of the system.

Where parts of the system are implanted remote from the clitoris, a second area remote from the first area may be dissected free in order to place e.g. the at least one reservoir in the patient's body at the remote second area, with a conduit connecting the reservoir with the at least one infusion needle accommodated in the at least one housing. In this case, it is preferable to place the reservoir adjacent the patient's symphyseal bone.

One or more of the following elements may be placed within the patient's body remote from the housing or housings accommodating the at least one needle:
- at least part of the drive unit D,
- the reservoir $R_1$, $R_2$,
- the pump P,
- at least one motor M, $M_2$ for actuation of the drive unit D or a drive driving the drive unit, and/or the pump P or any other energy consuming part of the system,
- energy storage means A for providing the at least one motor with energy,
- galvanic coupling elements between either an external energy source E or the energy storage means A and the motor M, $M_2$ for transmitting energy to the motor in contacting fashion,
- wireless coupling elements adapted to connect either the motor M, $M_2$ or the energy storage means A or both to an extracorporal primary energy source for transmitting energy to either the motor or the energy storage means or both in non-contacting fashion,
- control unit C1 for controlling the motor M, $M_2$,
- a data transmission interface for wirelessly transmitting data from an external data processing device $C_2$ to the control unit $C_1$,
- the feedback sensor F,
- wireless energy transforming means, and
- the injection port 32 for refilling the reservoir $R_1$.

The invention claimed is:

1. A female stimulation system for stimulating sexually responsive tissue of the vulva, in particular an erection or lubrication stimulation system, comprising a fully implantable drug delivery device for delivering a drug in relation to the female's sexually responsive tissue of the vulva to achieve sexual stimulation thereof, wherein the drug delivery device comprises at least one infusion needle adapted to be placed outside the corpora cavernosa in close proximity thereto, and
   a) wherein the at least one infusion needle is adapted to change position outside the corpora cavernosa, when the drug delivery device is implanted, and wherein the drug delivery device is further adapted to deliver drugs through the infusion needle outside the corpora cavernosa, when the needle's position is changed outside the corpora cavernosa, or
   b) wherein the infusion needle is adapted to be advanced into and retracted from at least one corpus cavernosum, when the drug delivery device is implanted, and wherein the drug delivery device is further adapted to deliver drugs through the infusion needle into the corpus cavernosum, whenever the needle is advanced into the corpus cavernosum.

2. The system of claim 1, adapted to stimulate an erectile tissue part of the sexually responsive tissue of the vulva to achieve engorgement of blood causing erection of the erectile tissue.

3. The system of claim 1, adapted to stimulate a lubrication part of the sexually responsive tissue of the vulva to achieve lubrication of sexually responsive tissue of the vulva.

4. The system of claim 2, adapted to stimulate the nerval system of the sexually responsive tissue of the vulva to achieve engorgement of blood causing erection of the erectile tissue or to achieve stimulation of the lubrication part of the sexually responsive tissue of the vulva causing lubrication of sexually responsive tissue of the vulva.

5. The system of claim 1, wherein the drug delivery device comprises at least one catheter adapted to be implanted outside the corpora cavernosa in close proximity thereto and wherein the drug delivery device is further adapted to supply drugs through the catheter.

6. The system of claim 1, wherein the drug delivery device comprises at least one catheter adapted to be implanted in at least one corpus cavernosum and wherein the drug delivery device is further adapted to supply drugs into the corpus cavernosum through the catheter.

7. The system of claim 1, wherein the at least one infusion needle has a tube-like body closed at the tip end and having a laterally arranged delivery exit port.

8. The system of claim 1,
   wherein the at least one infusion needle is disposed at least partly within at least one housing with a tip end of the at least one infusion needle arranged for penetrating the at least one housing's outer wall, the at least one housing being adapted for implantation inside a patient's body, and
   wherein at least one drive unit adapted for implantation inside the patient's body is provided, the at least one drive unit being coupled to the at least one infusion needle and arranged at least for advancing and retracting the tip end of the at least one infusion needle so that the at least one infusion needle penetrates, upon advancement of the tip end or ends thereof, said outer wall in at least one penetration area so as to allow for stimulation of erectile tissue by injecting the substance through said at least one penetration area via the at least one infusion needle.

9. The system of claim 8, wherein the drive unit is configured to laterally displace the tip end of at least one of said at least one infusion needle in at least two different lateral directions to different penetration sites within said at least one penetration area.

10. The system of claim 8, wherein the at least one infusion needle is arranged for penetrating the at least one housing's outer wall in at least two different penetration areas.

11. The system of claim 10, wherein the system is adapted such that the at least one infusion needle penetrates said at least two different penetration areas upon a single command or single action from the patient.

12. The system of claim 10, wherein the at least one drive unit is adapted for advancing and refracting the tip end of the at least one infusion needle in such way that it penetrates, upon advancement of the tip end or ends thereof, said at least two different penetration areas either simultaneously or in immediate time succession.

13. The system of claim 10, wherein the system is adapted such that the time delay between the penetration of a first and a second of said at least two different penetration areas does not exceed 120 seconds, and preferably does not exceed 60 seconds.

14. The system of claim 10, wherein the system is adapted such that once the at least one infusion needle has been refracted from a first of the at least two different penetration areas, advancement of the at least one infusion needle to a second of the at least two different penetration areas is initiated.

15. The system of claim 8, wherein at least in the penetration area or areas the outer wall is made from a material which is self-sealing in respect of penetrations resulting from said at least one infusion needle.

16. The system of claim 15, wherein the self-sealing material forms at least two window areas in said outer wall, said window areas being positioned for penetration by the tip end of the at least one infusion needle.

17. The system of claim 15, wherein the self-sealing material comprises a penetration membrane integrated in the outer wall by being sealingly press-fitted into the outer wall.

18. The system of claim 15, wherein the self-sealing material comprises at least one polymer selected from the group of materials comprising silicon and polyurethane.

19. The system of claim 1, wherein the at least one infusion needle is flexibly bendable, wherein the tip end of each of the at least one infusion needle is arranged for penetrating the outer wall of a first housing and the other end thereof is arranged in a second housing for remote implantation inside the patient's body, the injection needle being sufficiently long to bridge the distance from the second housing for remote implantation to the first housing and further through the first housing up to the outer wall of the first housing.

20. The system of claim 8, wherein the drive unit is configured to laterally displace the tip end of one infusion needle between two lateral positions such that the one infusion needle can penetrate the housing's outer wall in at least two different penetration areas, wherein the drive unit is configured to displace the tip end of the one infusion needle in at least one of; laterally to different penetration sites within each of said different penetration areas and at least two different lateral directions.

21. The system of claim 1, comprising at least one reservoir adapted for implantation inside the patient's body to store the drug to be delivered, wherein the reservoir comprises at least one first compartment accommodating or adapted to accommodate a first substance and at least one second compartment accommodating or adapted to accommodate a second substance, further comprising a mixing chamber for mixing the substance from the at least one first compartment with the substance from one or more of the at least one second compartment, wherein the substance contained in the at least one second compartment is in at least one of powder form and freeze-dried form.

22. The system of claim 1, further comprising at least one of: at least one pump (P) adapted for implantation inside the patient's body to advance the substance from the reservoir to the at least one infusion device and an actuating means for direct manual operation of a pump and/or the drive unit.

23. The system of claim 1, wherein at least one of; at least one motor is provided for actuating at least one of a pump, the drive unit and any other implantable energy consuming part of the system.

24. The system of claim 1, further comprising an energy source for providing energy to at least one of the pump, the drive unit and the motor, and any other energy consuming part of the system, wherein the system comprises coupling elements for wireless energy transfer from outside the patient's body to the energy storage means for charging the energy storage means from outside a patient's body, when the energy storage means is implanted in a patient's body, wherein at least one feedback sensor is provided and adapted to sense one or more physical parameters of the patient and/or process parameters of the system, further comprising a feedback subsystem adapted to wirelessly send feedback information relating to the energy to be stored in the energy storage means from inside the human body to the outside thereof, wherein the system is adapted to use the feedback information for adjusting the amount of wireless energy transmitted by the energy transmitter and/or adapted to provide feedback on parameters relevant for the treatment, including the one or more physical parameters of the patient and/or the process parameters of the system.

25. The system of claim 24, wherein the feedback information relates to an energy balance which is defined as at least one of; the balance between an amount of wireless energy received inside the human body and an amount of energy consumed by the at least one energy consuming part and a rate of wireless energy received inside the human body and a rate of energy consumed by the at least one energy consuming part.

* * * * *